US011890222B2

(12) United States Patent
Lin

(10) Patent No.: US 11,890,222 B2
(45) Date of Patent: Feb. 6, 2024

(54) DEVICE FOR ALLEVIATING OBSTRUCTIVE SLEEP APNEA

(71) Applicant: GOOD NEWS MEDICAL CO., LTD., Keelung (TW)

(72) Inventor: Chin-Chi Lin, Keelung (TW)

(73) Assignee: GOOD NEWS MEDICAL CO., LTD., Keelung (TW)

( * ) Notice: Subject to any disclaimer, the term of this patent is extended or adjusted under 35 U.S.C. 154(b) by 311 days.

(21) Appl. No.: 17/324,936

(22) Filed: May 19, 2021

(65) Prior Publication Data

US 2021/0361471 A1 Nov. 25, 2021

(30) Foreign Application Priority Data

May 21, 2020 (CN) .......................... 202010434944.5
Jun. 18, 2020 (CN) .......................... 202010557839.0
Jul. 17, 2020 (CN) .......................... 202010689937.X
Aug. 25, 2020 (CN) .......................... 202010860414.7
Sep. 30, 2020 (CN) .......................... 202011054578.7

(51) Int. Cl.
*A61F 5/56* (2006.01)

(52) U.S. Cl.
CPC .................................. *A61F 5/566* (2013.01)

(58) Field of Classification Search
CPC ...... A61F 5/56; A61F 5/566; A61F 2005/563; A61C 7/36; A61C 7/08; A61C 7/00; A63B 71/085; A63B 71/08; A63B 2071/086; A63B 2071/088; A61M 16/049; A61M 16/0488; A61M 16/0493; A61M 16/0495; A61M 16/0497; A61M 1/74; A61M 1/741;

(Continued)

(56) References Cited

U.S. PATENT DOCUMENTS 4,169,473 A 10/1979 Samelson
4,196,724 A 4/1980 Wirt et al.
4,198,967 A 4/1980 Dror (Continued)

FOREIGN PATENT DOCUMENTS

CN 102133141 B 1/2013
CN 102144946 B 7/2013

(Continued)

*Primary Examiner* — Michelle J Lee
*Assistant Examiner* — Robin Han
(74) *Attorney, Agent, or Firm* — Muncy, Geissler, Olds & Lowe, P.C.

(57) ABSTRACT

A device for alleviating obstructive sleep apnea includes: a base fixed to a user's head and having a passage; a suction member having a channel passing through the passage to enter the user's oral cavity and move within the passage, with the channel connected to a tongue fixing portion disposed at the tip of the user's tongue, wherein the suction member has a stopping portion disposed outside the oral cavity to limit forward displacement of the tongue fixing portion; a resilient element for providing the tongue fixing portion with an elastic force required to approach the base and being weaker than a suction force between the suction member and the tongue and weaker than a pulling force generated by the tongue in tongue motion; and a negative pressure source communicating with the channel to provide negative pressure to the tongue in contact with the tongue fixing portion.

18 Claims, 29 Drawing Sheets

(58) Field of Classification Search
CPC .. A61M 1/80; A61M 1/71; A61M 1/81; Y10S 602/902
USPC .................. 128/848, 859, 860, 861, 862
See application file for complete search history.

(56) References Cited

U.S. PATENT DOCUMENTS

| | | | |
|---|---|---|---|
| 5,373,859 A | 12/1994 | Forney | |
| 6,494,209 B2 | 12/2002 | Kulick | |
| 7,328,698 B2 * | 2/2008 | Scarberry | ......... A61M 16/0493 128/200.24 |
| 7,607,439 B2 | 10/2009 | Li | |
| 7,918,222 B2 | 4/2011 | Chen | |
| 8,028,705 B2 | 10/2011 | Li | |
| 8,074,656 B2 | 12/2011 | Vaska et al. | |
| 8,091,554 B2 | 1/2012 | Jiang | |
| 8,122,889 B2 | 2/2012 | Vaska et al. | |
| 8,122,890 B2 | 2/2012 | Vaska | |
| 8,387,620 B1 | 3/2013 | Vaska et al. | |
| 8,402,973 B2 | 3/2013 | Podmore et al. | |
| 8,505,540 B2 | 8/2013 | Vaska et al. | |
| 8,567,406 B2 | 10/2013 | Chen et al. | |
| 8,573,223 B2 | 11/2013 | Podmore et al. | |
| 8,613,283 B2 | 12/2013 | Hegde et al. | |
| 8,616,208 B2 | 12/2013 | Chen et al. | |
| 8,656,922 B2 | 2/2014 | Vaska et al. | |
| 8,667,970 B2 | 3/2014 | Podmore et al. | |
| 8,701,672 B2 | 4/2014 | Vaska | |
| 8,857,439 B2 | 10/2014 | Hegde et al. | |
| 8,979,823 B2 | 3/2015 | Podmore et al. | |
| 9,101,495 B2 | 8/2015 | McAnelly et al. | |
| 9,101,498 B2 | 8/2015 | Podmore et al. | |
| 9,138,342 B2 | 9/2015 | Chen et al. | |
| 9,241,825 B2 | 1/2016 | Vaska et al. | |
| 9,339,620 B2 | 5/2016 | Chen et al. | |
| 9,375,541 B2 | 6/2016 | Vitale et al. | |
| 9,387,117 B2 | 7/2016 | Chen et al. | |
| 9,387,118 B2 | 7/2016 | Vaska et al. | |
| 9,387,119 B2 | 7/2016 | Podmore | |
| 9,483,792 B2 | 11/2016 | Podmore et al. | |
| 9,549,795 B2 | 1/2017 | Podmore et al. | |
| 9,610,190 B2 | 4/2017 | Vaska et al. | |
| 9,655,768 B2 | 5/2017 | Vaska et al. | |
| 9,763,759 B2 | 9/2017 | Vitale et al. | |
| 10,080,855 B2 | 9/2018 | Chen et al. | |
| 10,117,773 B2 | 11/2018 | Podmore | |
| 10,149,782 B2 | 12/2018 | Chen et al. | |
| 10,149,783 B2 | 12/2018 | Chen et al. | |
| 10,159,595 B2 | 12/2018 | Chen et al. | |
| 10,166,140 B2 | 1/2019 | Chen et al. | |
| 10,245,175 B2 | 4/2019 | Podmore et al. | |
| 10,426,905 B2 | 10/2019 | Vaska et al. | |
| D871,571 S | 12/2019 | Chen et al. | |
| 10,646,671 B2 | 5/2020 | Vaska et al. | |
| 2001/0047805 A1 | 12/2001 | Scarberry | |
| 2004/0211430 A1 | 10/2004 | Pivovarov | |
| 2005/0166928 A1 | 8/2005 | Jiang | |
| 2005/0166929 A1 | 8/2005 | Jiang | |
| 2011/0180076 A1 | 7/2011 | Hegde et al. | |
| 2011/0192404 A1 | 8/2011 | Chen | |
| 2011/0265801 A1 | 11/2011 | Cullen | |
| 2012/0024297 A1 * | 2/2012 | Hegde | ................ A61F 5/566 128/848 |
| 2013/0263865 A1 | 10/2013 | Khast | |
| 2014/0190489 A1 | 7/2014 | Chen et al. | |
| 2015/0342778 A1 | 12/2015 | Chen et al. | |
| 2019/0015618 A1 | 1/2019 | Chen et al. | |

FOREIGN PATENT DOCUMENTS

| | | |
|---|---|---|
| CN | 103961201 A | 8/2014 |
| CN | 102028574 B | 9/2014 |
| CN | 103140192 B | 3/2015 |
| CN | 103976814 B | 1/2016 |
| CN | 103989550 B | 1/2016 |
| CN | 101917924 B | 3/2016 |
| CN | 104000680 B | 4/2016 |
| CN | 103687568 B | 5/2016 |
| CN | 104519841 B | 5/2016 |
| CN | 105748187 A | 7/2016 |
| CN | 103717181 B | 8/2016 |
| CN | 205494125 U | 8/2016 |
| CN | 104540480 B | 9/2016 |
| CN | 104427958 B | 7/2017 |
| CN | 106170272 B | 6/2018 |
| CN | 108742882 A | 11/2018 |
| CN | 208552192 U | 3/2019 |
| CN | 105726192 B | 9/2019 |
| CN | 110352046 A | 10/2019 |
| TW | I353831 B | 12/2011 |
| TW | I396526 B | 5/2013 |
| TW | I421106 B | 1/2014 |
| TW | I448279 B | 8/2014 |
| TW | I499408 B | 9/2015 |
| TW | I503134 B | 10/2015 |
| TW | I505846 B | 11/2015 |
| TW | I541035 B | 7/2016 |
| TW | I542337 B | 7/2016 |
| TW | 201637677 A | 11/2016 |
| TW | I566749 B | 1/2017 |
| TW | I678199 B | 12/2019 |
| WO | WO2019101213 A1 | 5/2019 |

* cited by examiner

DEVICE FOR ALLEVIATING OBSTRUCTIVE SLEEP APNEA

BACKGROUND

1. Technical Field

The present disclosure relates to devices for alleviating obstructive sleep apnea and, more particularly, to a device for alleviating obstructive sleep apnea by pulling a user's tongue outward.

2. Description of the Related Art

Obstructive sleep apnea, a common sleep disorder, is especially associated with the supine sleeping position, as the tongue and soft palate relax to block the airway temporarily, thereby cutting off breathing for brief periods of time. Due to the presence of gravity and the relaxation of human tissue, the tongue falls backward, and the soft palate collapses, leading to blockage of the upper airway. Blockage of the upper airway during sleep causes dyspnea and snoring and may even be life-threatening.

Conventional treatments for obstructive sleep apnea include immobilizing the tongue with pliers or applying negative pressure to keep the tongue at a non-collapsed position, i.e., preventing tongue collapse with an external mechanical device. The mechanical device-based treatment has an advantage: it spares patients the side effects of medications and surgical lesions.

However, the conventional mechanical device-based treatment of pulling the front end of the user's tongue out of his/her oral cavity with pliers or applying negative pressure is effective in precluding tongue collapse, although the excessive pulling on the tongue entail a considerable chance of causing the user discomfort. Furthermore, the mechanical device-based treatment entails fixing the user's tongue at a non-collapsed position; as a result, the user wearing the device cannot move the tongue appropriately, leading to tongue fatigue and inability of the user to use the tongue to assist with the swallowing of saliva. Once an excessive amount of saliva accumulates, the user's respiration will be affected.

Therefore, it is imperative to provide an improved device for alleviating obstructive sleep apnea with a view to overcoming the aforesaid drawbacks of the prior art.

SUMMARY

In view of the aforesaid drawbacks of the prior art, it is an objective of the present disclosure to provide a device for pulling a user's tongue outward without preventing appropriate movement of the user's tongue.

In order to achieve the above and other objectives, the present disclosure provides:

A device for alleviating obstructive sleep apnea comprises: a base fitted and fixed to a user's head and having a passage; a suction member having a channel extending and passing through the passage to enter the user's oral cavity and undergo displacement within the passage, with the channel connected to a tongue fixing portion, the tongue fixing portion being disposed at a front end of the user's tongue, wherein the suction member has a stopping portion for limiting forward displacement of the tongue fixing portion; a resilient element for providing the tongue fixing portion with an elastic force required to approach the base, the elastic force being both weaker than a suction force between the suction member and the user's tongue and weaker than a pulling force generated by the user's tongue in tongue motion; a negative pressure source in communication with the channel and providing a negative pressure to the user's tongue in contact with the tongue fixing portion; and an adjustment element disposed outside the user's oral cavity, connected to the base, and capable of moving forward and rearward relative to the base, wherein the stopping portion is disposed on the outer surface of the suction member, limited by the adjustment element, and adapted to limit the forward displacement of the tongue fixing portion.

Furthermore, the tongue fixing portion has an air inlet, the air inlet being disposed on the inner surface of the tongue fixing portion, facing the user's tongue, and being in communication with the channel, and the negative pressure acts on the front end of the user's tongue through the air inlet, thereby allowing at least a portion of the user's tongue to attach to the inner surface of the tongue fixing portion.

Furthermore, the tongue fixing portion has a receiving space in communication with the channel such that the user's tongue is at least partially received in the receiving space, starting from the front end of the user's tongue.

Furthermore, a concave space is formed at the rear end of the tongue fixing portion to accommodate a lingual frenulum of the user.

Furthermore, the tongue fixing portion comprises two said concave spaces disposed on the upper side and the lower side of the tongue fixing portion, respectively.

Furthermore, the resilient element directly exerts a forward elastic force on the suction member, and indirectly exerts a reward elastic force on the base.

Furthermore, the suction member comprises a connector in communication with the channel and the negative pressure source, and the resilient element has an end exerting a force on the adjustment element and another end exerting a force on the connector.

Furthermore, the connector, the resilient element and the channel are at least partially received in the adjustment element simultaneously.

Furthermore, the resilient element fits around the channel, and at least part of the resilient element is closer to the adjustment element than is the channel so as to prevent the resilient element from interfering with the channel.

Furthermore, the connector and the channel are connected by threads.

Furthermore, the stopping portion is disposed at the connector.

Furthermore, the base comprises an outer expansion portion disposed outside the user's oral cavity, and the outer expansion portion is of dimensions greater than the dimensions of the user's mouth.

Furthermore, the outer expansion portion has a plurality of perforations penetrating an outer surface of the outer expansion portion, away from the user's face and penetrating an inner surface of the outer expansion portion, facing the user's face.

Furthermore, the outer expansion portion abuts against the user's face except for the user's lips and comprises a main body adapted to cover the user's face and a pad disposed on the main body, the pad being disposed between the main body and the user's face when in use, wherein the pad is elastically stretched and contracted relative to the main body.

Furthermore, the resilient element is received in the adjustment element and, the resilient element has an end connected to the adjustment element and another end fixed to the suction member, wherein the extent to which the resilient element is stretched or compressed remains unchanged in the course of forward and rearward movement of the adjustment element relative to the base.

Furthermore, the adjustment element comprises a screw portion received in the passage, the screw portion being penetrated in a front-rear direction so as to receive the resilient element and a portion of the suction member, and the rear end of the resilient element exerts a force on the rear end of the screw portion, wherein the adjustment element further comprises an operating cap fixed to the front end of the screw portion such that the stopping portion and the operating cap abut against each other.

Furthermore, the tongue fixing portion moves in a direction perpendicular to a front-rear direction and in directions other than perpendicular to the front-rear direction.

Furthermore, the transverse cross section area of a bore of the channel decreases toward the user's tongue to prevent the user's tongue from entering the bore of the channel under the suction force.

Compared with the prior art, the present disclosure has advantages as follows: the user's tongue is fixed in place by the negative pressure provided by the negative pressure source and the suction member to minimize the chance of the user's discomfort; owing to the stopping portion, the device prevents the user's tongue from collapsing without pulling the user's tongue beyond the user's lips, so as to preclude the user's discomfort, which might otherwise be caused by excessive pulling on the user's tongue. Furthermore, the resilient element prevents the collapse of the user's tongue while allowing the user to appropriately move the tongue, such as moving the tongue rearward to facilitate the swallowing of saliva and thereby preventing the accumulation of saliva. After the user has finished moving the tongue, the device is effective in automatically restoring the tongue to a non-collapsed position under an elastic force generated by the resilient element.

A device for alleviating obstructive sleep apnea, applicable to the user's head, the device comprising: a base fitted and fixed to the user's head and having a passage; a suction member having a hollow-cored channel extending and passing through the passage to enter the user's oral cavity and undergo displacement within the passage, with the channel connected to a tongue fixing portion, the tongue fixing portion being cup-shaped and thus matching the user's tongue in terms of outline, forming a receiving space in communication with the channel and adapted to enclose and receive the user's tongue, wherein the suction member further has a stopping portion disposed outside the user's oral cavity to limit forward displacement of the tongue fixing portion, wherein the tongue fixing portion is adapted to, under a negative pressure, adsorb to the front end of the tongue and fittingly surround the transverse outline of the user's tongue to form a hermetic seal, such that the negative pressure acts only on the user's tongue, wherein the tongue fixing portion is adapted to move freely together with the user's tongue within the user's oral cavity, wherein, when the user's tongue relaxes, the tongue fixing portion drives the user's tongue to move forward until the stopping portion stops moving, a resilient element for providing the tongue fixing portion with an elastic force required to approach the base, the elastic force being not only weaker than a suction force between the suction member and the user's tongue but also weaker than a pulling force generated by the user's tongue in tongue motion; a negative pressure source in communication with the channel and adapted to provide negative pressure to the user's tongue in contact with the tongue fixing portion; and an adjustment element disposed outside the user's oral cavity, connected to the base, and capable of moving forward and rearward relative to the base, wherein the resilient element is received in the adjustment element, and the resilient element has an end connected to the adjustment element, wherein the extent to which the resilient element is stretched or compressed remains unchanged in the course of forward and rearward movement of the adjustment element relative to the base.

A device for alleviating obstructive sleep apnea comprises: a base fitted and fixed to a user's head and having a passage; a suction member having a channel extending and passing through the passage to enter the user's oral cavity and undergo displacement within the passage, with the channel connected to a tongue fixing portion, the tongue fixing portion being disposed at a front end of the user's tongue, wherein the suction member has a stopping portion for limiting forward displacement of the tongue fixing portion; a resilient element for providing the tongue fixing portion with an elastic force required to approach the base, the elastic force being both weaker than a suction force between the suction member and the user's tongue and weaker than a pulling force generated by the user's tongue in tongue motion; a negative pressure source in communication with the channel and providing a negative pressure to the user's tongue in contact with the tongue fixing portion; and an adjustment element disposed outside the user's oral cavity, connected to the base, and capable of moving forward and rearward relative to the base, wherein the resilient element is received in the adjustment element, and the resilient element has an end connected to the adjustment element, wherein the extent to which the resilient element is stretched or compressed remains unchanged in the course of forward and rearward movement of the adjustment element relative to the base.

Furthermore, the tongue fixing portion has an air inlet, the air inlet being disposed on the inner surface of the tongue fixing portion, facing the user's tongue, and being in communication with the channel, and the negative pressure acts on the front end of the user's tongue through the air inlet, thereby allowing at least a portion of the user's tongue to attach to the inner surface of the tongue fixing portion.

Furthermore, the tongue fixing portion has a receiving space in communication with the channel, such that the user's tongue is at least partially received in the receiving space, starting from the front end of the user's tongue.

Furthermore, a concave space is formed at the rear end of the tongue fixing portion to accommodate a lingual frenulum of the user.

Furthermore, the tongue fixing portion comprises two said concave spaces disposed on the upper side and the lower side of the tongue fixing portion, respectively.

Furthermore, the resilient element directly exerts a forward elastic force on the suction member, and indirectly exerts a reward elastic force on the base.

Furthermore, the suction member comprises a connector in communication with the channel and the negative pressure source, and the resilient element has an end exerting a force on the adjustment element and another end exerting a force on the connector.

Furthermore, the connector, the resilient element and the channel are at least partially received in the adjustment element simultaneously.

Furthermore, the resilient element fits around the channel, and at least part of the resilient element is closer to the adjustment element than is the channel so as to prevent the resilient element from interfering with the channel.

Furthermore, the connector and the channel are connected by threads.

Furthermore, the stopping portion is disposed at the connector.

Furthermore, the base comprises an outer expansion portion disposed outside the user's oral cavity, and the outer expansion portion is of dimensions greater than the dimensions of the user's mouth.

Furthermore, the outer expansion portion has a plurality of perforations penetrating an outer surface of the outer expansion portion, away from the user's face, and penetrating an inner surface of the outer expansion portion, facing the user's face.

Furthermore, the outer expansion portion abuts against the user's face except for the user's lips and comprises a main body adapted to cover the user's face and a pad disposed on the main body, the pad being disposed between the main body and the user's face when in use, wherein the pad is elastically stretched and contracted relative to the main body.

Furthermore, the adjustment element comprises a screw portion received in the passage, the screw portion being penetrated in a front-rear direction so as to receive the resilient element and a portion of the suction member, and the rear end of the resilient element exerts a force on the rear end of the screw portion, wherein the adjustment element further comprises an operating cap fixed to the front end of the screw portion such that the stopping portion and the operating cap abut against each other.

Furthermore, the tongue fixing portion moves in a direction perpendicular to a front-rear direction and in directions other than perpendicular to the front-rear direction.

Furthermore, the transverse cross-section area of a bore of the channel decreases toward the user's tongue to prevent the user's tongue from entering the bore of the channel under the suction force.

The stopping portion is disposed outside the user's oral cavity to simplify related structures of the device within the user's oral cavity, to reduce the volume of the related structures of the device within the user's oral cavity, lessen the sensation of a foreign body, and enhance the user's comfort. Furthermore, the driving mechanism prevents the collapse of the user's tongue while allowing the user to appropriately move the tongue, such as moving the tongue rearward to facilitate the swallowing of saliva and thereby preventing the accumulation of saliva. After the user has finished moving the tongue, the device is effective in automatically restoring the tongue to a non-collapsed position by the driving mechanism.

DETAILED DESCRIPTION OF THE EMBODIMENTS

Figure 1:
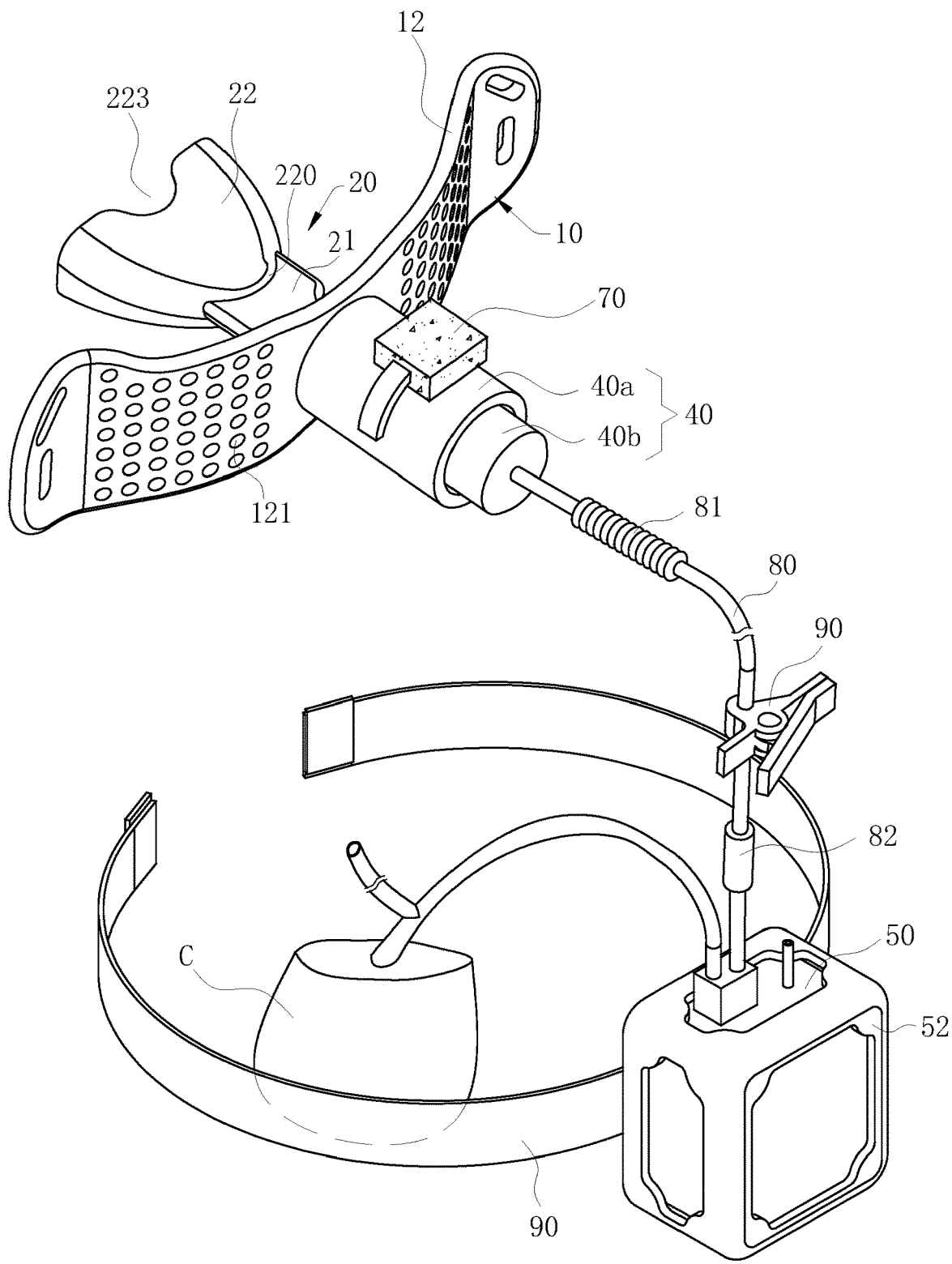
FIG. 1 is a schematic view of a device for alleviating obstructive sleep apnea according to the first embodiment of the present disclosure.

Objectives, structures, features, and advantages of the present disclosure are hereunder illustrated with specific embodiments, depicted with accompanying drawings, and described below.

Referring to FIG. 1 through FIG. 6, a device for alleviating obstructive sleep apnea, which is provided in the first embodiment of the present disclosure, comprises a base 10 fitted and fixed to a user's head, a suction member 20 for applying suction to the user's tongue T, a driving mechanism joined to the base 10 and the suction member 20, two adjustment elements 40 for adjusting an elastic force of the driving mechanism, and a negative pressure source 50 for providing the suction member 20 with a negative pressure under which the suction member 20 applies suction to the user's tongue T. The two adjustment elements 40 are a first adjustment element 40*a* and a second adjustment element 40*b*, respectively, and are disposed outside the user's oral cavity. The first adjustment element 40*a* is connected to the base 10. The second adjustment element 40*b* is connected to the suction member 20. In this embodiment, the suction member 20 functions as a tongue puller, whereas the driving mechanism is a resilient element 30 provided in the form of a spring. For the sake of illustration, the user's head functions as a system of direction references, with the user's face facing forward, the top of the user's head facing upward, and the user's left ear facing leftward.

Figure 3:
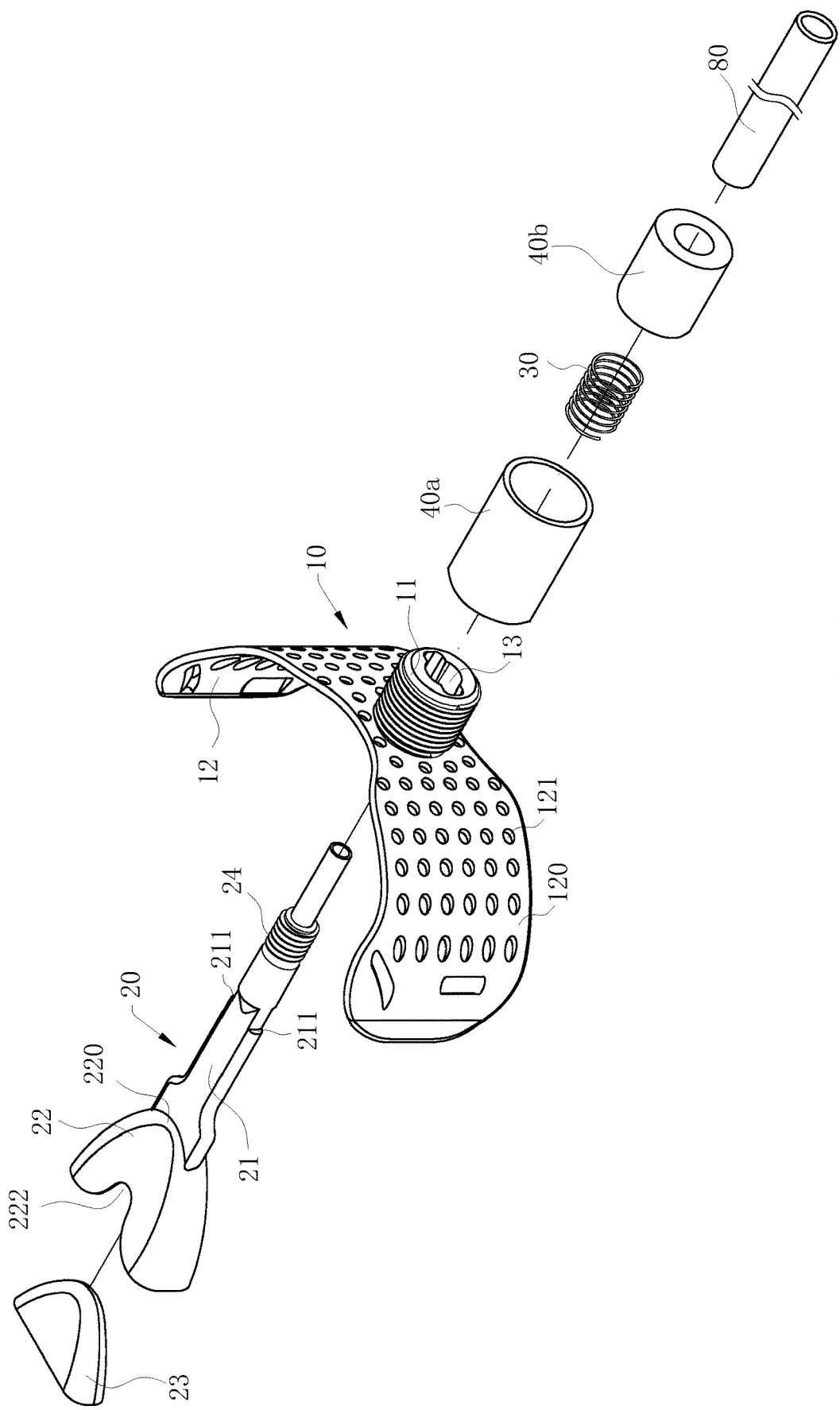
FIG. 3 is a partial exploded view of the device of FIG. 1.

Referring to FIG. 3, the base 10 has a cylindrical portion 11, an outer expansion portion 12 connected to the cylindrical portion 11 from behind, and a passage 13 extending forward to penetrate the cylindrical portion 11 and rearward to penetrate the outer expansion portion 12. The cylindrical portion 11 extends forward, i.e., extends away from the outer expansion portion 12.

Figure 2:
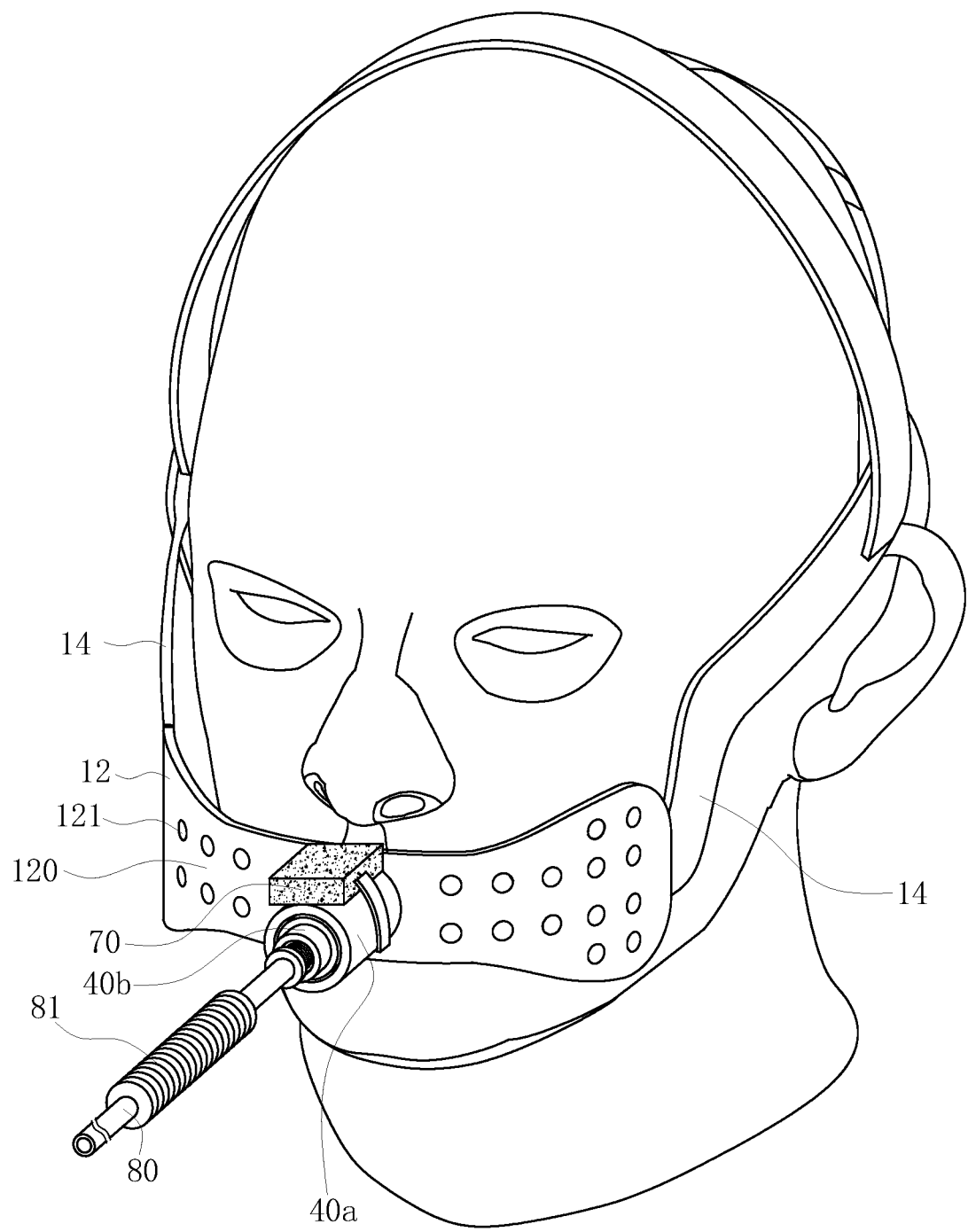
FIG. 2 is a schematic view which shows that part of the device of FIG. 1 is fixed to a user's head.
Figure 5:
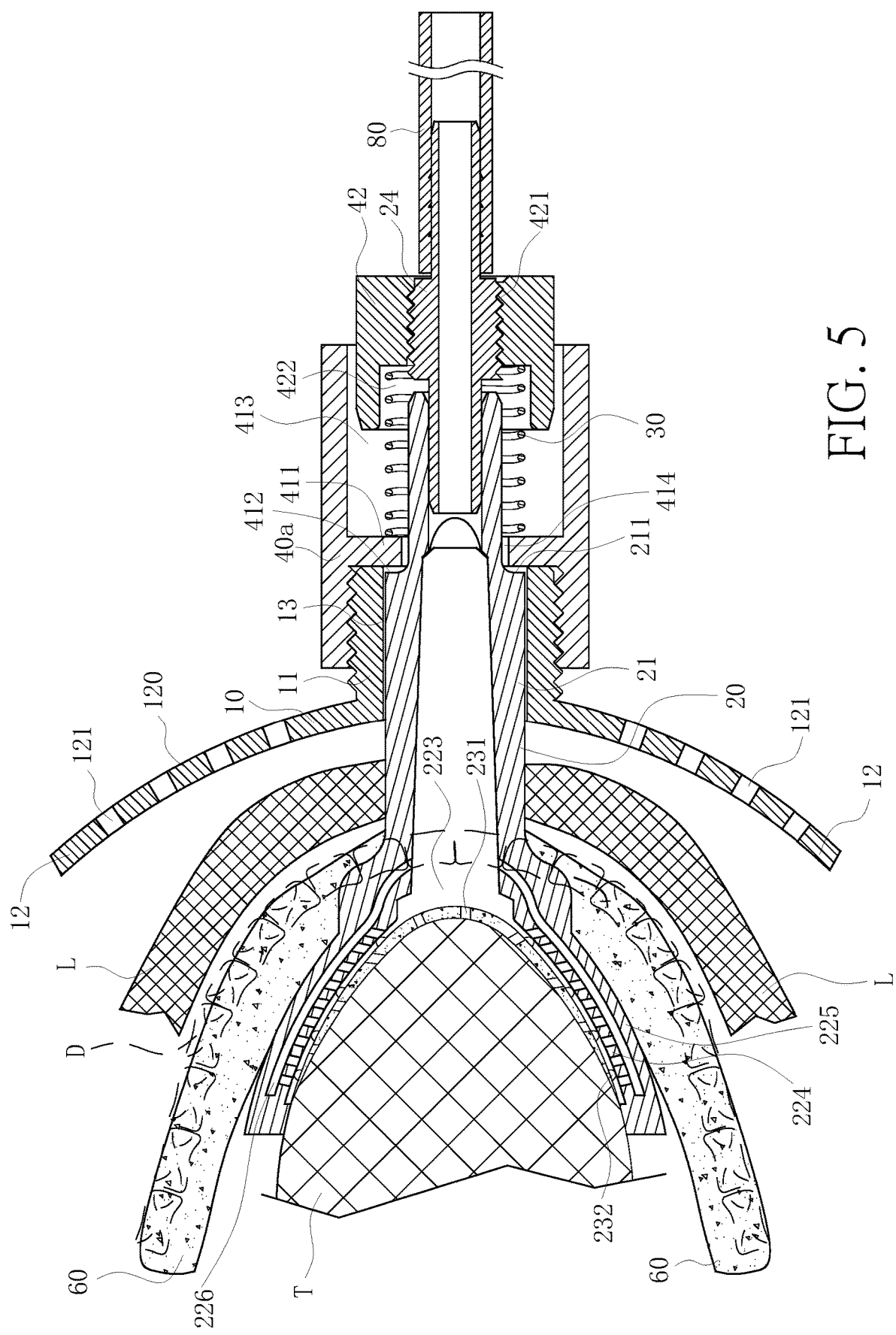
FIG. 5 is a schematic view which shows that a suction member of the device of FIG. 4 is fixed to the user's tongue and pulls the tongue.

Referring to FIG. 2 and FIG. 5, the base 10 must be fixed in place relative to the user's head in order for the device to function. In this embodiment, the outer expansion portion 12 has a main body 120 extending leftward and rightward from the cylindrical portion 11, adapted to directly abut against the user's face except for the user's lips L, and intended to prevent the base 10 from moving rearward to maintain the position of the base 10. To prevent the outer expansion portion 12 from hermetically sealing the user's mouth, the main body 120 of the outer expansion portion 12 has a plurality of perforations 121. The perforations 121 penetrate the outer expansion portion 12 and thus are exposed from the outer and inner surfaces thereof; thus, in addition to through the nose, the user can breathe through the oral cavity. The inner surface of the outer expansion portion 12 faces the user's face. The outer surface of the outer expansion portion 12 faces away from the user's face. The outer expansion portion 12 is curved and resilient in order to match the user's face in terms of outline and maximize the contact area therebetween, thereby distributing the pressure imposed by the outer expansion portion 12 on the user's face. To couple the base 10 and the user's head together further firmly, two fixing elements 14 are connected to the left and right ends of the outer expansion portion 12, respectively. In this embodiment, the fixing elements 14 are cords, and the user's is head surrounded by the fixing elements 14 and the outer expansion portion 12, such that the base 10 is tied to the front of the user's mouth. The fixing elements 14 pull the left and right ends of the outer expansion portion 12, respectively, such that the outer expansion portion 12 matches the user's face better in terms of outline. In another embodiment, the fixing elements 14 provided in the form of cords hang on the user's ears, respectively. In a variant embodiment, the outer expansion portion 12 and the fixing elements 14 are not required.

Figure 4:
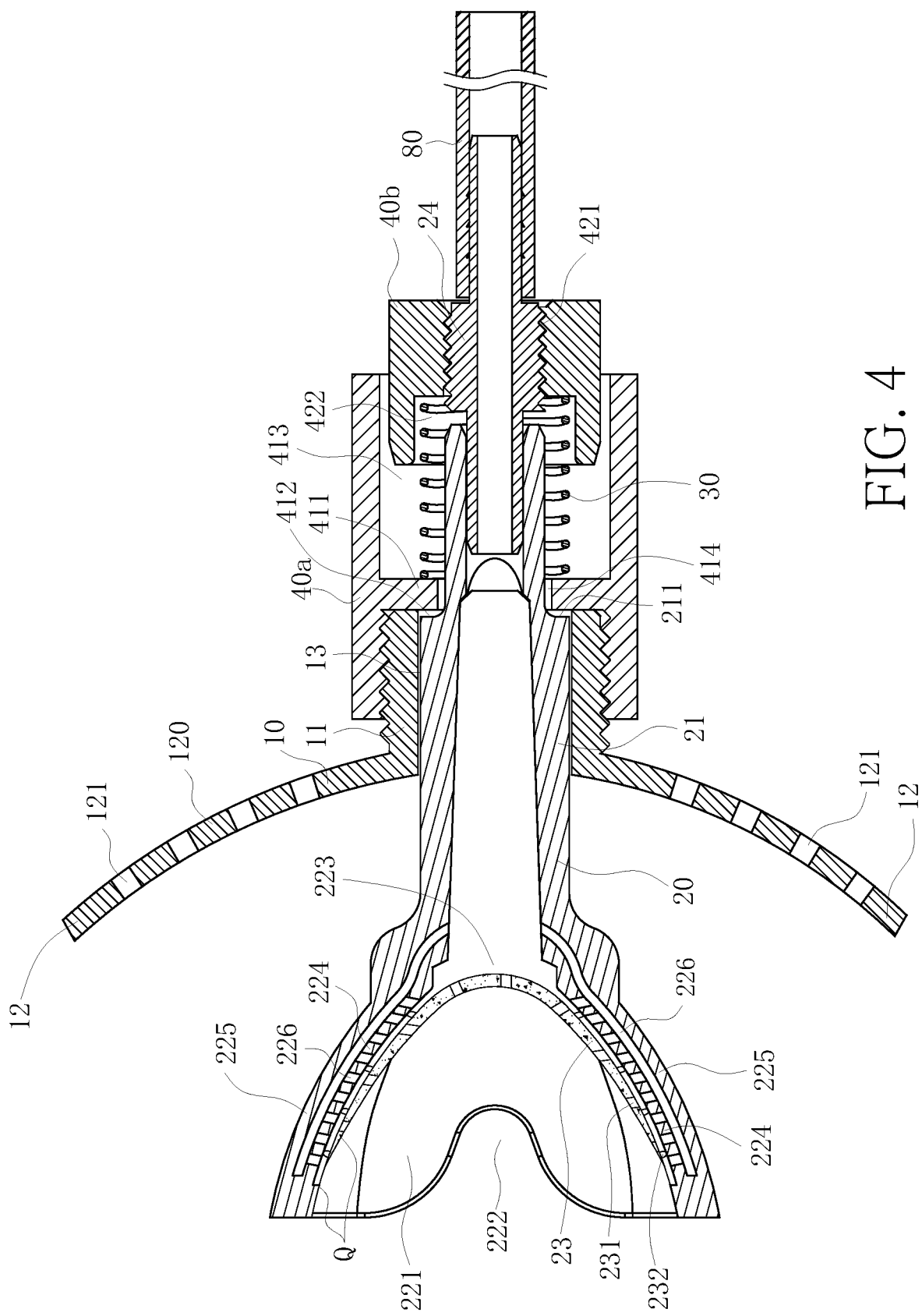
FIG. 4 is a cross-sectional view of the device assembled according to FIG. 3.

Referring to FIG. 3 and FIG. 4, the outer surface of the cylindrical portion 11 has an external thread whereby the cylindrical portion 11 is fitted to the first adjustment element 40a.

Figure 6:
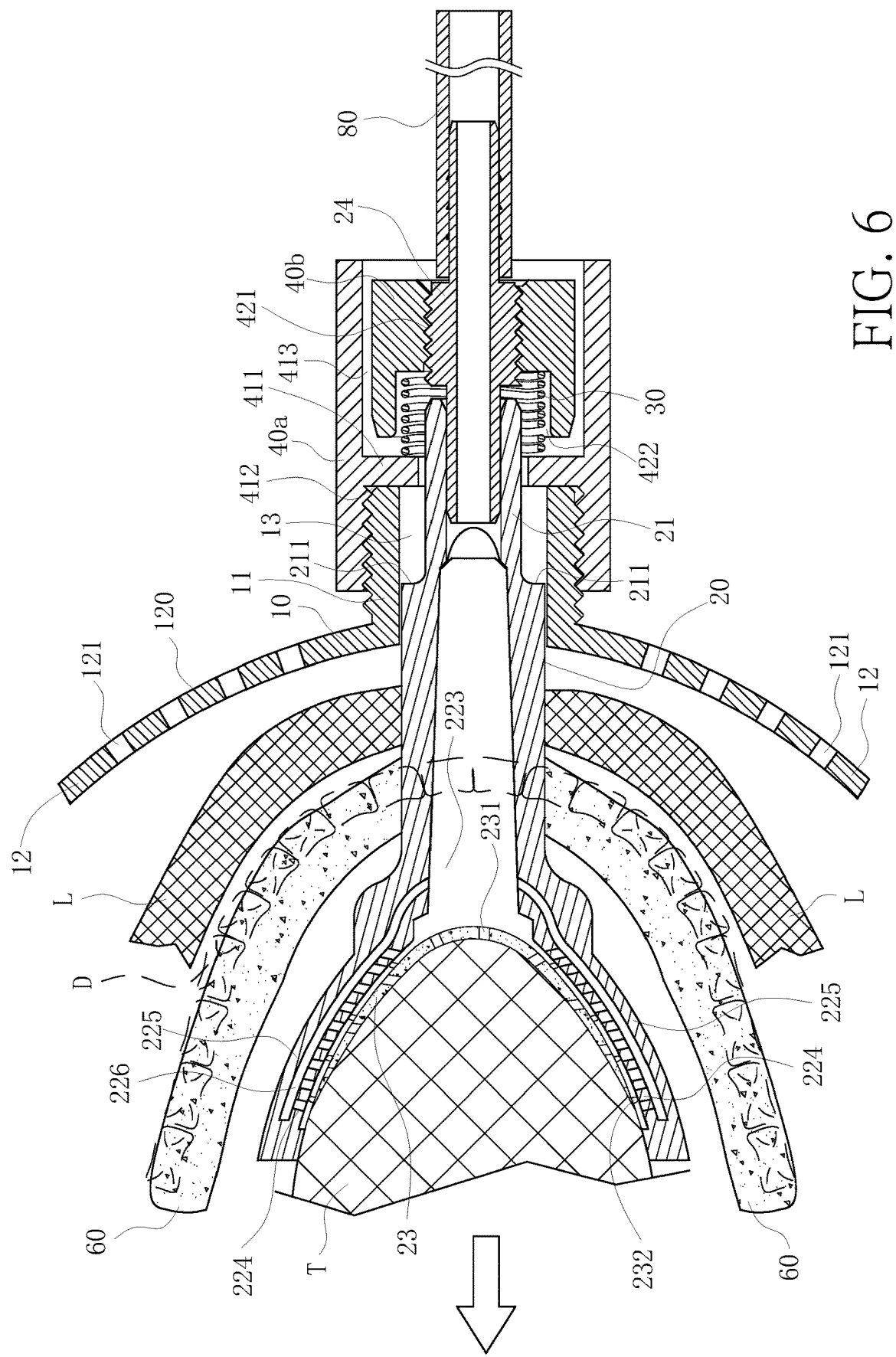
FIG. 6 is a schematic view which shows that the suction member of the device of FIG. 4 is fixed to the user's tongue and the user moves the tongue backward.

Referring to FIG. 1, FIG. 5 and FIG. 6, the suction member 20 moves forward and rearward relative to the base 10. As shown in the diagrams, the suction member 20 comprises a channel 21 and a tongue fixing portion 22 connected to the channel 21. The channel 21 extends and passes through the passage 13 to enter the user's oral cavity and thus transfer the negative pressure generated by the negative pressure source 50 to the user's oral cavity; hence, the negative pressure is applied to the user's tongue T only, and the channel 21 undergoes displacement within the passage 13.

Referring to FIG. 3 through FIG. 6, the suction member 20 has at least one stopping portion. In this embodiment, the outer surface of the channel 21 has one said stopping portion, which is defined as the first stopping portion 211. The first stopping portion 211 is fitted to the first adjustment element 40a to limit the outward (i.e., forward) displacement of the tongue fixing portion 22. The tongue fixing portion 22 expands in all directions relative to the channel 21, and thus it is also feasible for the stopping portion to be disposed at the front end of the tongue fixing portion 22; hence, the stopping portion is defined as the second stopping portion 220, which serves to limit the outward (i.e., forward) displacement of the tongue fixing portion 22. Specifically, the second stopping portion 220 is not only disposed on the upper side and the lower side of the junction of the tongue fixing portion 22 and the channel 21 but is also stopped at the inner side of the user's upper teeth D or lower teeth D as a result of the movement of the tongue fixing portion 22 so as to limit the outward (i.e., forward) displacement of the tongue fixing portion 22. One of the first stopping portion 211 and the second stopping portion 220 limits the outward (i.e., forward) displacement of the tongue fixing portion 22 while the device is operating. In a variant embodiment, both of the first stopping portion 211 and the second stopping portion 220 are provided on the suction member 20; or one of a first stopping portion 211 and a second stopping portion 220 is provided on the suction member 20.

Referring to FIG. 1, FIG. 4 and FIG. 5, in this embodiment, the tongue fixing portion 22 is made of a soft material which is comfortable to the human body, such as silicone. The tongue fixing portion 22 is cup-shaped and thus matches the user's tongue T in terms of outline. The tongue fixing portion 22 has a receiving space 221 which opens rearward to receive the front end of the user's tongue T when the device is in use. Two concave spaces 222 for receiving the user's labial frenulum, respectively, are disposed at the rear end of the tongue fixing portion 22 and disposed on the upper side and the lower side of the tongue fixing portion 22, respectively. Furthermore, one said concave 222 is disposed below the receiving space 221, whereas the other concave 222 is disposed above the receiving space 221. Owing to the symmetric arrangement of the two concave spaces 222, the user need not give considerations to the upward and downward orientation of the tongue fixing portion 22 while operating the device. An air inlet 223 is disposed on the inner surface of the receiving space 221, that is, the inner surface (facing the user's tongue T) of the tongue fixing portion 22. The receiving space 221 is in communication with the channel 21 through the air inlet 223. Therefore, when the device is in use, the negative pressure is ultimately transferred into the receiving space 221 and applied to the user's tongue T received in the receiving space 221, thereby allowing the user's tongue T to be adsorbable and fixed to the tongue fixing portion 22. The tongue fixing portion 22 fittingly surrounds the transverse outline of the user's tongue T to form a hermetic seal. The transverse outline is the outline of the transverse cross section of the user's tongue T. The negative pressure is transmitted to the interior of the receiving space 221 but not to the entire oral cavity. Furthermore, the receiving space 221 receives the user's tongue T only, and thus the negative pressure acts on the user's tongue T but not on the other parts of the user's head. In another embodiment, the tongue fixing portion 22 is cup-shaped or pocket-shaped and thus matches the user's tongue T in terms of outline, but the tongue fixing portion 22 may also be plate-shaped to match the upper surface of the user's tongue T in terms of outline, and its lower surface has a plurality of said air inlets 223.

Referring to FIG. 4 through FIG. 6, in this embodiment, the tongue fixing portion 22 comprises an inner layer 224 positioned proximate to the user's tongue T and an outer layer 225 positioned distal to the user's tongue T. The inner layer 224 and the outer layer 225 are integrally formed by injection molding. In another embodiment, the inner layer 224 and the outer layer 225 are formed separately and then assembled together, and the inner layer 224 is made of a softer material than that of the outer layer 225 to render the tongue fixing portion 22 comfortable. Alternatively, the inner layer 224 is thinner than the outer layer 225, such that the inner layer 224 is softer than the outer layer 225. The tongue fixing portion 22 has therein a plurality of micro-channels 226. The micro-channels 226 are disposed at the inner layer 224 and between the inner layer 224 and the outer layer 225. The micro-channels 226 penetrate the inner and outer surfaces of the inner layer 224, and are in communication with the channel 21 and the receiving space 221. The micro-channels 226 are exposed from the inner surface of the tongue fixing portion 22 and in the vicinity of the air inlets 223. The diameter of the micro-channels 226 is less than the diameter of the air inlets 223. Therefore, instead of being concentrated on a small area of the user's tongue T and causing the user discomfort, the negative pressure acting on the user's tongue T is widely distributed to enable the user to relax.

Referring to FIG. 4 through FIG. 6, a protective pad 23 is disposed on one of the surfaces of the tongue fixing portion 22 to allow the protective pad 23 to face the inner surface of the user's tongue T. Owing to the protective pad 23, a user will find the device comfortable even if the user's tongue T is tactilely sensitive. The protective pad 23 is made of a soft material, such as acrylic foam or silicone, and has a plurality of through holes 231, which are fine and distributed densely. There is no step between the inner surface of the tongue fixing portion 22 and the inner surface of the protective pad 23, and thus they jointly form a continuous curved surface Q. The curved surface Q matches the user's tongue T in terms of outline. When the device is in use, the protective pad 23 is placed in the receiving space 221 beforehand to enable a new user to change the protective pad 23. After the user's tongue T has protruded into the receiving space 221, the protective pad 23 is stretched according to the shape of the user's tongue T. There is no step between the inner surface of the tongue fixing portion 22 and the inner surface of the protective pad 23, and thus they jointly form a continuous curved surface Q. The curved surface Q matches the user's tongue T in terms of outline and encloses the front end of the user's tongue T. The user's tongue T is spaced apart from the air inlets 223 and the micro-channels 226. The negative pressure is transmitted through the through holes 231 of the protective pad 23; thus, the negative pressure acting on the user's tongue T is further decreased, thereby rendering the device comfortable. A gap in communication with the channel 21 is formed between the outer side of the protective pad 23 and the inner side of the tongue fixing portion 22. In this embodiment, the outer surface of the protective pad 23 has a plurality of bump dots 232 protruding toward the inner surface of the tongue fixing portion 22. The bump dots 232 abut against the inner surface of the tongue fixing portion 22. Thus, gaps in communication with the air inlets 223 are formed between the outer surface of the protective pad 23 and the inner surface of the tongue fixing portion 22 and between the plurality of bump dots 232, such that the negative pressure can be transmitted through the through holes 231 of the protective pad 23. However, in a variant embodiment (not shown), the protective pad 23 is fixed to the inner surface of the tongue fixing portion 22, and the bump dots 232 are disposed on the inner surface of the tongue fixing portion 22. However, the aforesaid embodiments are not restrictive of the present disclosure.

When the negative pressure acts on the front end of the user's tongue T in the absence of the protective pad 23, the user's tongue T attaches to the inner surface of the tongue fixing portion 22, and the front end of the user's tongue T hermetically seals the air inlets 223 and the micro-channels 226. In the presence of the protective pad 23, the user's tongue T attaches to the inner surface of the protective pad 23, and the front end of the user's tongue T hermetically seals the through holes 231 of the protective pad 23. In another embodiment, the transverse cross section area of the bore of the channel 21 decreases toward the user's tongue T, that is, in the vicinity of the air inlets 223 the user's tongue T is prevented from entering into the bore of the channel 21 under the suction force to cause the user discomfort. The channel 21 thus branches off in a tapered manner to form a plurality of parallel fine-channels or becomes flat with a linear cross section.

Referring to FIG. 3 and FIG. 4, the suction member 20 comprises a connector 24 disposed at the front end of the suction member 20. The connector 24 lies outside the base 10 and has one end fixedly connected to the channel 21. The connector 24 is tubular. In this embodiment, the connector 24 and the channel 21 are formed separately. One end of the connector 24 fits to the terminal end of the channel 21 to serve interfering and fixing purposes. An external thread is disposed on the outer surface at the middle of the connector 24 such that the connector 24 is fitted to the second adjustment element 40b. No thread is disposed at the two ends of the connector 24. In a variant embodiment (not shown), the connector 24 and the channel 21 are integrally formed and connected. However, the aforesaid embodiments are not restrictive of the present disclosure.

Referring to FIG. 4 through FIG. 6, the first adjustment element 40a is cylindrical and comprises a baffle 411, a receiving chamber 412 disposed behind the baffle 411 and penetrating rearward, and a receiving cavity 413 disposed in front of the baffle 411 and penetrating forward. An internal thread is disposed on the inner surface of the receiving chamber 412. The external thread of the cylindrical portion 11 meshes with the internal thread of the receiving chamber 412; thus, it is only when the user rotates the first adjustment element 40a that the first adjustment element 40a moves forward and rearward relative to the base 10. The receiving cavity 413 not only receives the resilient element 30 but also receives the second adjustment element 40b when the suction member 20 moves relative to the base 10. The baffle 411 has a penetrating hole 414 which penetrates the baffle 411 in the front-rear direction of the first adjustment element 40a. The penetrating hole 414 penetrates rearward to communicate with the receiving chamber 412 and forward to communicate with the receiving cavity 413. The channel 21 passes through the penetrating hole 414 of the baffle 411 to enter the receiving cavity 413. The baffle 411, which is disposed in front of the first stopping portion 211 to stop the first stopping portion 211, limits how deeply the channel 21 can enter the receiving cavity 413 and limits the outward (i.e., forward) displacement of the tongue fixing portion 22 connected to the channel 21. Therefore, the user controls the maximum outward displacement of the tongue fixing portion 22 by moving the first adjustment element 40a in the front-rear direction. In particular, the forward movement of the first adjustment element 40a causes the forward movement of the baffle 411 and thus increases the room for the first stopping portion 211 to move, thereby increasing the maximum outward displacement of the tongue fixing portion 22. Conversely, the rearward movement of the first adjustment element 40a causes the rearward movement of the baffle 411 and thus decreases the room for the first stopping portion 211 to move, thereby decreasing the maximum outward displacement of the tongue fixing portion 22. Furthermore, the baffle 411, which is disposed in front of the cylindrical portion 11 to stop the cylindrical portion 11, limits how deeply the cylindrical portion 11 can enter the receiving chamber 412 or, in other words, the rearward adjustment of the first adjustment element 40a.

Referring to FIG. 4 and FIG. 6, the second adjustment element 40b has a first hole 421 and a second hole 422 connected to the rear end of the first hole 421. The second hole 422 is of a greater size than the first hole 421. The internal thread disposed on the inner surface of the first hole 421 meshes with the external thread disposed on the outer surface of the connector 24; thus, it is only when the user rotates the second adjustment element 40b that the second adjustment element 40b moves forward and rearward relative to the connector 24 such that the second hole 422 contains the resilient element 30. In this embodiment, the overall dimensions of the second adjustment element 40b are less than the dimensions of the receiving cavity 413 such that the second adjustment element 40b is received in the receiving cavity 413 and moves relative thereto when the first adjustment element 40a and the second adjustment element 40b undergo displacement relative to each other. In another embodiment (not shown), the dimensions of the second hole 422 are greater than the overall dimensions of the first adjustment element 40a, such that the first adjustment element 40a is contained in the second hole 422 when the first adjustment element 40a and the second adjustment element 40b undergo displacement relative to each other. However, the aforesaid embodiments are not restrictive of the present disclosure.

Referring to FIG. 3 through FIG. 6, in this embodiment, the resilient element 30 is a compression spring. The resilient element 30 fits around a portion of channel 21 which protrude forward beyond the base 10, and the resilient element 30 is received in the receiving cavity 413 and the second hole 422. One end of the resilient element 30 is in front of and abuts against the front end surface of the baffle 411. The other end of the resilient element 30 forwardly and directly abuts against the wall of the second hole 422 of the second adjustment element 40b. In another embodiment, the resilient element 30 exerts an elastic force on the first adjustment element 40a and the second adjustment element 40b by any other means of connection, such as fixing the resilient element 30 to the first adjustment element 40a and the second adjustment element 40b by screws. When the device is in use, the resilient element 30 is compressed by the first adjustment element 40a and the second adjustment element 40b and thus generates elastic forces in opposite directions, respectively. Thus, the resilient element 30 not only exerts on the first adjustment element 40a a rearward elastic force which is transmitted to the base 10 but also exerts on the second adjustment element 40b a forward elastic force which is transmitted to the suction member 20 via the connector 24 so as to cause the suction member 20 to move forward relative to the base 10, drive the forward movement of the user's tongue T fixed to the tongue fixing portion 22, keep the front end of the user's tongue T away from the user's soft palate and throat under the elastic forces, and ultimately prevent obstructive sleep apnea otherwise caused by the collapse of the user's tongue T. When the device is in use, the second stopping portion 220 and the user's teeth D abut against each other, or the first stopping portion 211 and the baffle 411 abut against each other, thereby preventing the tongue fixing portion 22 and the user's tongue T from protruding beyond the user's lips L.

When the device is in use, the user is already in or ready to enter a sleeping state; meanwhile, the user's tongue T is certainly slack. Thus, the device is designed to cope with the user's slack tongue T. The elastic force provided by the resilient element 30 is intended only to be sufficient to pull the user's slack tongue T rather than intended to stop the user from overcoming the elastic force in order for the user to move the tongue T. In this regard, the user can move the tongue T by muscular activity, ruling out a collapsed tongue typical of a relaxed user. When the user is using the device, the elastic force is not only weaker than a suction force between the suction member 20 and the user's tongue T but also weaker than a pulling force generated by the user's tongue T by muscular activity. Owing to the muscular activity of the user's tongue T, the tongue fixing portion 22 moves freely within the user's oral cavity. When the user's tongue T is slack, the tongue fixing portion 22 drives the forward movement of the user's tongue T until the first stopping portion 211 is stopped. Normally, saliva is continuously secreted in the user's oral cavity. To swallow his/her saliva, the user is likely to move the tongue T rearward, whether consciously or subconsciously. Thus, the device in use does not prevent the user from swallowing his/her saliva consciously or subconsciously, and thus accumulation of saliva is reduced to a certain degree.

It is possible that the user may experience discomfort caused by the second stopping portion 220 abutting against the user's teeth D or by an excessive elastic force acting on the tongue T. Referring to FIG. 4 through FIG. 6, the user can rotate at least one of the first adjustment element 40a and the second adjustment element 40b and thus change the extent of compression of the resilient element 30 being compressed by the first adjustment element 40a and the second adjustment element 40b so as to change the elastic force provided by the resilient element 30. In this embodiment, the pitch of the thread of the first adjustment element 40a is greater than the pitch of the thread of the second adjustment element 40b, such that the displacement in the front-rear direction of the first adjustment element 40a because of a complete turn thereof is greater than the displacement in the front-rear direction of the second adjustment element 40b because of a complete turn thereof, thereby enabling different levels of adjustment precision.

Another embodiment requires only one, rather than both, of the first adjustment element 40a and the second adjustment element 40b, for example, the first adjustment element 40a, such that one end of the resilient element 30 is joined to the first adjustment element 40a and positioned proximate to the user's oral cavity, whereas the other end of the resilient element 30 is joined to the connector 24 and positioned distal to the user's oral cavity. A variant embodiment provides the second adjustment element 40b instead of the first adjustment element 40a, such that one end of the resilient element 30 is joined to the base 10 and positioned proximate to the user's oral cavity, whereas the other end of the resilient element 30 is joined to the second adjustment element 40b and positioned distal to the user's oral cavity. In another embodiment, the resilient element 30 is not necessarily a compression spring but can be a tension spring or resilient rubber washer in the presence of an elastic force under which the user's tongue T is pulled outward.

Referring to FIG. 5 and FIG. 6, the device further has an occlusion portion 60. The occlusion portion 60 is disposed on the outer side of the tongue fixing portion 22 and transversely extends in the direction of the alignment of the user's teeth D. The occlusion portion 60 is of greater hardness than the tongue fixing portion 22 and is positioned between the user's upper teeth D and lower teeth D when in use, such that the user bites the occlusion portion 60; thus, it is impossible for the tongue fixing portion 22 to be directly bitten by the user and thus for the tongue T to be hurt. The occlusion portion 60 fits to the channel 21, and the suction member 20 moves forward and rearward relative to the occlusion portion 60. Alternatively, the occlusion portion 60 protrudes from the base 10 toward the interior of the user's oral cavity. Alternatively, the occlusion portion 60 and the tongue fixing portion 22 are integrally formed and connected, the occlusion portion 60 extends from the outer surfaces of the left and right sides of the suction member 20, while the occlusion portion 60 and the tongue fixing portion 22 are made of two different materials, respectively.

Referring to FIG. 1 through FIG. 3, to inform the user or a nurse of the therapeutic benefits of the device, the device further has a breath sensor 70 disposed above the first adjustment element 40a and adapted to measure and record physiological parameters related to breathing, such as breath frequency, breath strength, and snore level. The user or nurse determines whether the negative pressure level previously used and the elastic force provided by the resilient element 30 can achieve the predetermined therapeutic benefits of the device and adjusts them according to the parameters recorded.

Referring to FIG. 1, the suction member 20 and the negative pressure source 50 are connected by a flexible connection pipe 80. In an embodiment, the connection pipe 80 has a flexible portion 81 positioned proximate to the channel 21 and adapted to enable the user to temporarily increase the length of the connection pipe 80 in order to change sleeping position, so as to prevent the connection pipe 80 from being stretched tight and thus exerting an excessive force on the user's tongue T. The flexible portion 81 is a corrugated pipe, a highly-ductile hose, or a coil formed by winding the connection pipe 80 helically.

Referring to FIG. 1, the connection pipe 80 further has a non-return valve 82 for ensuring that air current will flow in a unidirectional manner from the tongue fixing portion 22 to the negative pressure source 50, i.e., ensuring that the negative pressure will be transmitted in a unidirectional manner from the negative pressure source 50 to the tongue fixing portion 22.

Figure 7:
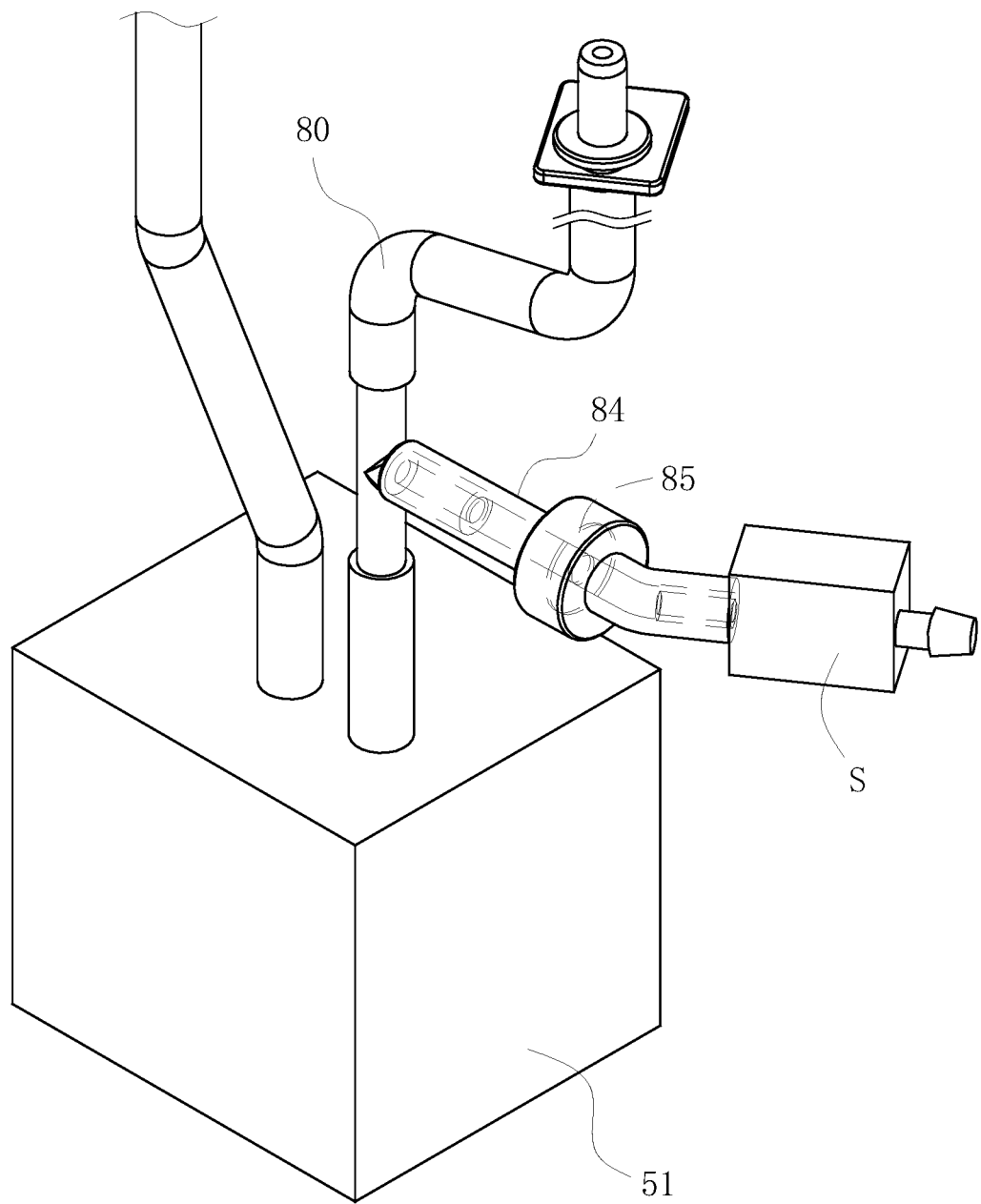
FIG. 7 is a schematic view of a connection pipe, air pressure sensor and vacuum pump in the negative pressure source of FIG. 1.

Referring to FIG. 1 and FIG. 7, the negative pressure source 50 comprises a conventional electric vacuum pump 51 for extracting air to generate the negative pressure. The connection pipe 80 extends into the negative pressure source 50 and connects to the vacuum pump 51 such that the suction member 20 is in direct communication with the vacuum pump 51, thereby allowing the negative pressure generated by the vacuum pump 51 to be directly transmitted to the channel 21 and the tongue fixing portion 22. In another embodiment, the negative pressure is generated by a positive pressure air pump which supplies a continuous air current to another airway. The channel 21 is in communication with the airway via a unidirectional valve and thus functions as a bypass for the airway. The unidirectional valve only allows air to flow from the channel 21 to the airway. The continuous air current creates a low air pressure in the airway. The air in the channel 21 flows to the airway via the unidirectional valve such that there is negative pressure in the channel 21 and the tongue fixing portion 22.

Figure 8:
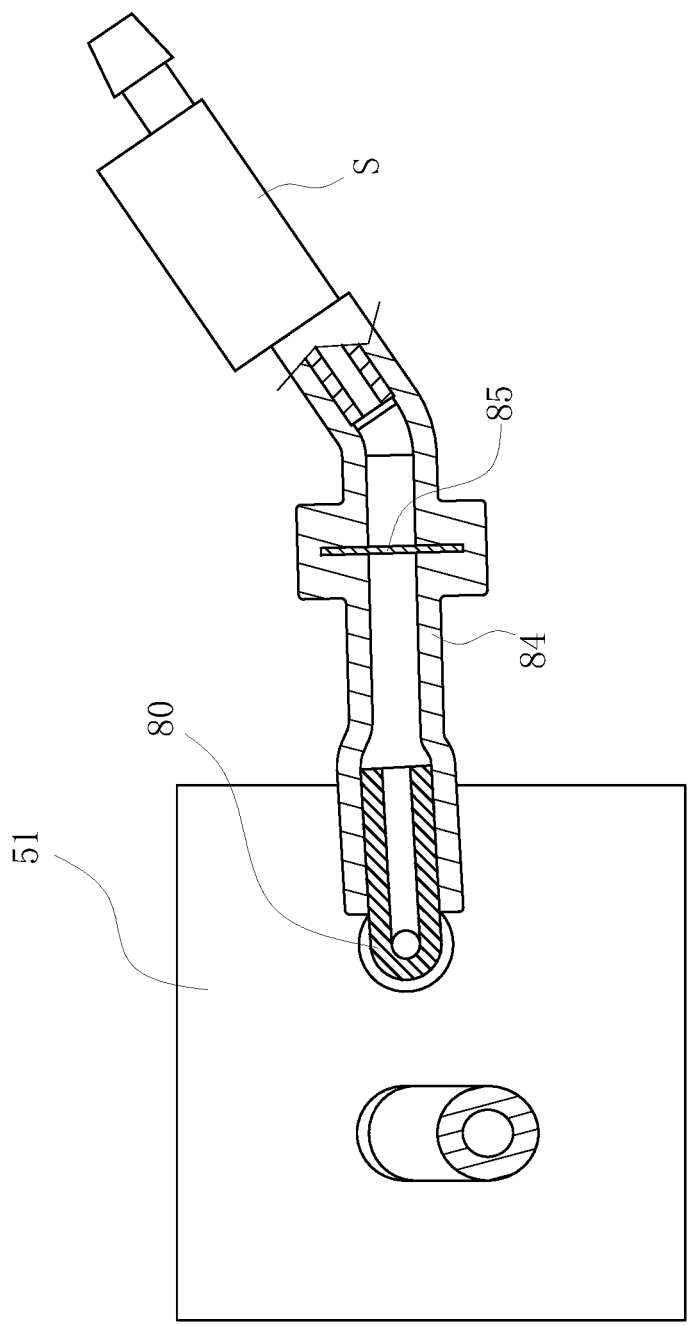
FIG. 8 is a cross-sectional view based on FIG. 7.

Referring to FIG. 1, numerous parts and components are connected between the negative pressure source 50 the suction member 20, and they have manufacturing tolerance. Furthermore, wear and tear will cause deviation between the user's tongue and the tongue fixing portion 22 and deviation between the parts and components when mounted in place. As a result, the operating device's actual air tightness level will be lower than its experimental air tightness level. To keep the negative pressure at a predetermined level, the device further comprises an air pressure sensor S provided in the form of a commercially-available, conventional, small-sized air pressure sensor. In this embodiment, the air pressure sensor S is disposed in the negative pressure source 50. As shown in FIG. 7 and FIG. 8, the connection pipe 80 comprises a main tube in communication with the vacuum pump 51 and the suction member 20 and a branch tube 84 in communication with the main tube and the air pressure sensor S. The air pressure sensor S detects the air pressure level in the negative pressure source 50 and sends data related to the detected air pressure level to a control unit (not shown). The control unit adjusts the operating power of the vacuum pump 51 according to the air pressure level, increasing the operating power of the vacuum pump 51 when the air pressure level is lower than a predetermined value, and decreasing the operating power of the vacuum pump 51 when the air pressure level is greater than another predetermined value. In another embodiment, the air pressure sensor S is in communication with the channel 21.

Referring to FIG. 7 and FIG. 8, in this embodiment, to prevent the air pressure sensor S from being affected by liquid and moisture (i.e., droplets suspended in air, as opposed to gaseous water molecules) in the connection pipe 80 or the channel 21, the branch tube 84 has therein a waterproofing element 85. The dimensions of the waterproofing element 85 are greater than the inner diameter of the branch tube 84 to ensure that the waterproofing element 85 can cover the cross section of the branch tube 84 completely and can be inserted into the wall of the branch tube 84 by an insert molding process so as to ensure the liquid tightness at the junction of the waterproofing element 85 and the branch tube 84. The branch tube 84, inclusive of the waterproofing element 85, is formed separately from the connection pipe 80 and then mounted on the main tube of the connection pipe 80. In a variant embodiment, with a binder, the waterproofing element 85 is adhered to the branch tube 84 from inside.

In this embodiment, the waterproofing element 85 is provided in the form of Goretex® film. The Goretex® material is waterproof but permeable to air and is widely applicable to products for use in outdoor activities. Given the high air-permeability of the waterproofing element 85 made of Goretex® film, air pressure variation taking place in the connection pipe 80 is propagated to the space between the waterproofing element 85 and the air pressure sensor S; thus, the air pressure sensor S directly senses the air pressure variation taking place in the connection pipe 80 without being affected by the liquid and moisture in the connection pipe 80.

In another embodiment, the waterproofing element 85 is made of a material (for example, polyethylene) which is not only waterproof but also capable of preventing permeation of gas molecules. Furthermore, the waterproofing element 85 is not only film-shaped and thus of minimal thickness but also has sufficient resilience to deform in response to the air pressure difference between the two sides of the waterproofing element 85. As a result, the waterproofing element 85 is waterproof, airtight, lightweight, thin, and elastically deformable, such that the waterproofing element 85 can prevent the exchange of air currents between its two sides.

When the air pressures on the two sides of the waterproofing element 85 are equal, the waterproofing element 85 does not deform and thus remains flat. When the air pressure in the connection pipe 80 is lower than the air pressure between the waterproofing element 85 and the air pressure sensor S, the waterproofing element 85 deforms by protruding toward the connection pipe 80, whereas the space between the waterproofing element 85 and the air pressure sensor S enlarges to thereby cause a decrease in air pressure, thereby allowing the air pressure sensor S to indirectly detect data pertaining to a reduction of air pressure in the connection pipe 80. Conversely, when the air pressure in the connection pipe 80 is higher than the air pressure between the waterproofing element 85 and the air pressure sensor S, the waterproofing element 85 deforms by protruding toward the air pressure sensor S, whereas the space between is diminished to thereby cause an increase in air pressure, thereby allowing the air pressure sensor S to detect the air pressure between the waterproofing element 85 and the air pressure sensor S.

Referring to FIG. 1, the negative pressure source 50 further has a protective case 52 for enclosing its outer surface. The protective case 52 is made of leather or silicone and can cushion the negative pressure source 50 in operation from impacts to which it may be exposed.

Referring to FIG. 1, in this embodiment, the device further comprises a liquid-collecting mechanism C in communication with the connection pipe 80. The liquid-collecting mechanism C comprises a liquid-collecting bag for collecting saliva that accidentally flows into the connection pipe 80 via the suction member 20.

Referring to FIG. 1, in this embodiment, the device further comprises two fixing mechanisms 90. One said fixing mechanism 90 is a clip adapted to fit around the connection pipe 80. In practice, the user fixes the clip to a specific, reliable, stationary object to prevent the slender connection pipe 80 from swinging or being overly wound.

Referring to FIG. 1, the other fixing mechanism 90 is a band connected to the protective case 52 or held by the outer surfaces of the protective case 52 and the negative pressure source 50. The other fixing mechanism 90 surrounds the user's body and ties the negative pressure source 50 to the user's body.

Figure 9:
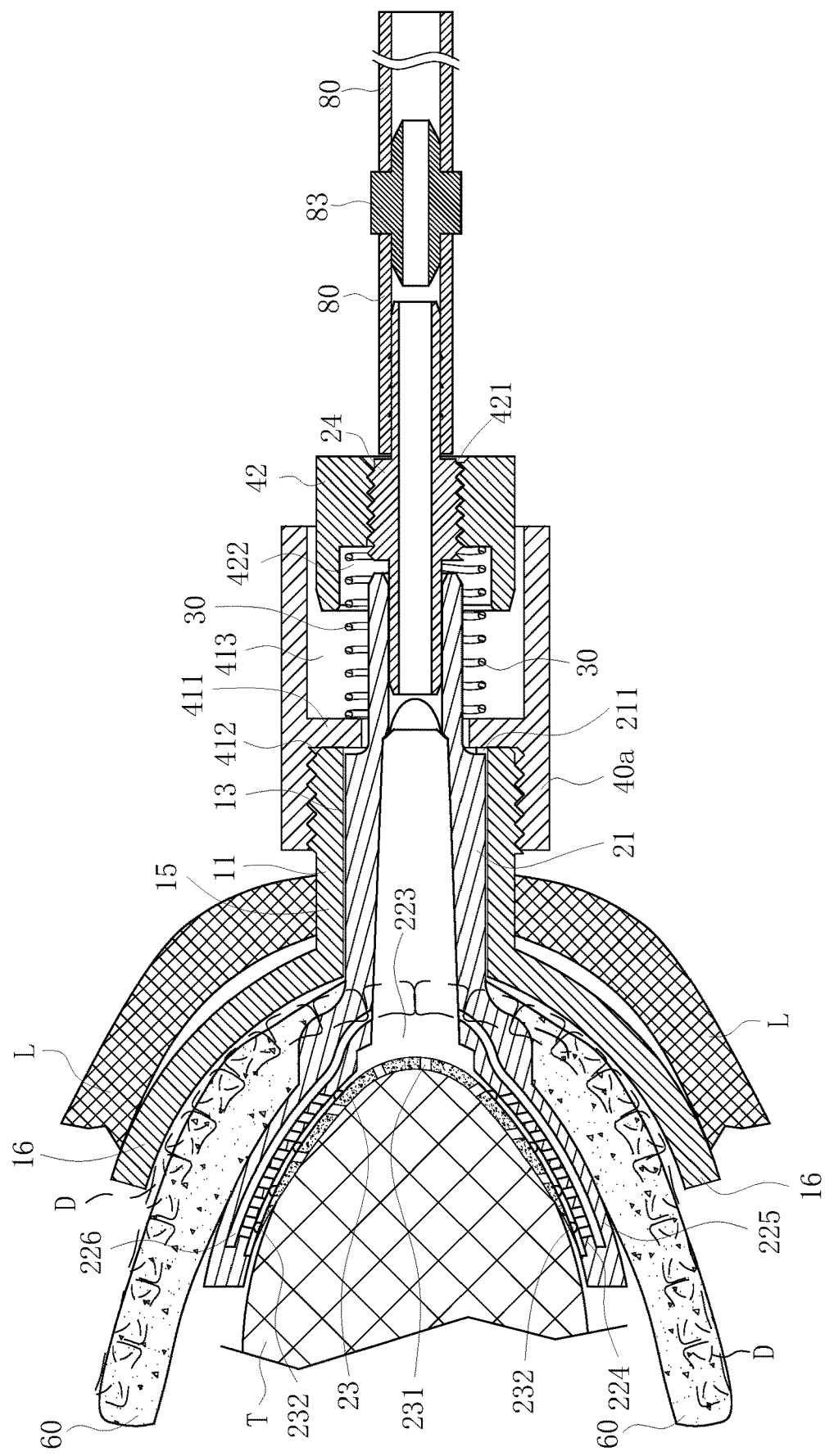
FIG. 9 is a schematic view of the device for alleviating obstructive sleep apnea according to the second embodiment of the present disclosure.

Referring to FIG. 9, the device for alleviating obstructive sleep apnea is provided according to the second embodiment of the present disclosure. Technical features which distinguish the second embodiment from the first embodiment are as follows: a portion of the base 10 must enter the user's oral cavity in order for the device to work, thereby necessitating a unique means for fixing the base 10 to the user's head and a unique means for preventing the connection pipe 80 from being stretched tight.

Figure 10:
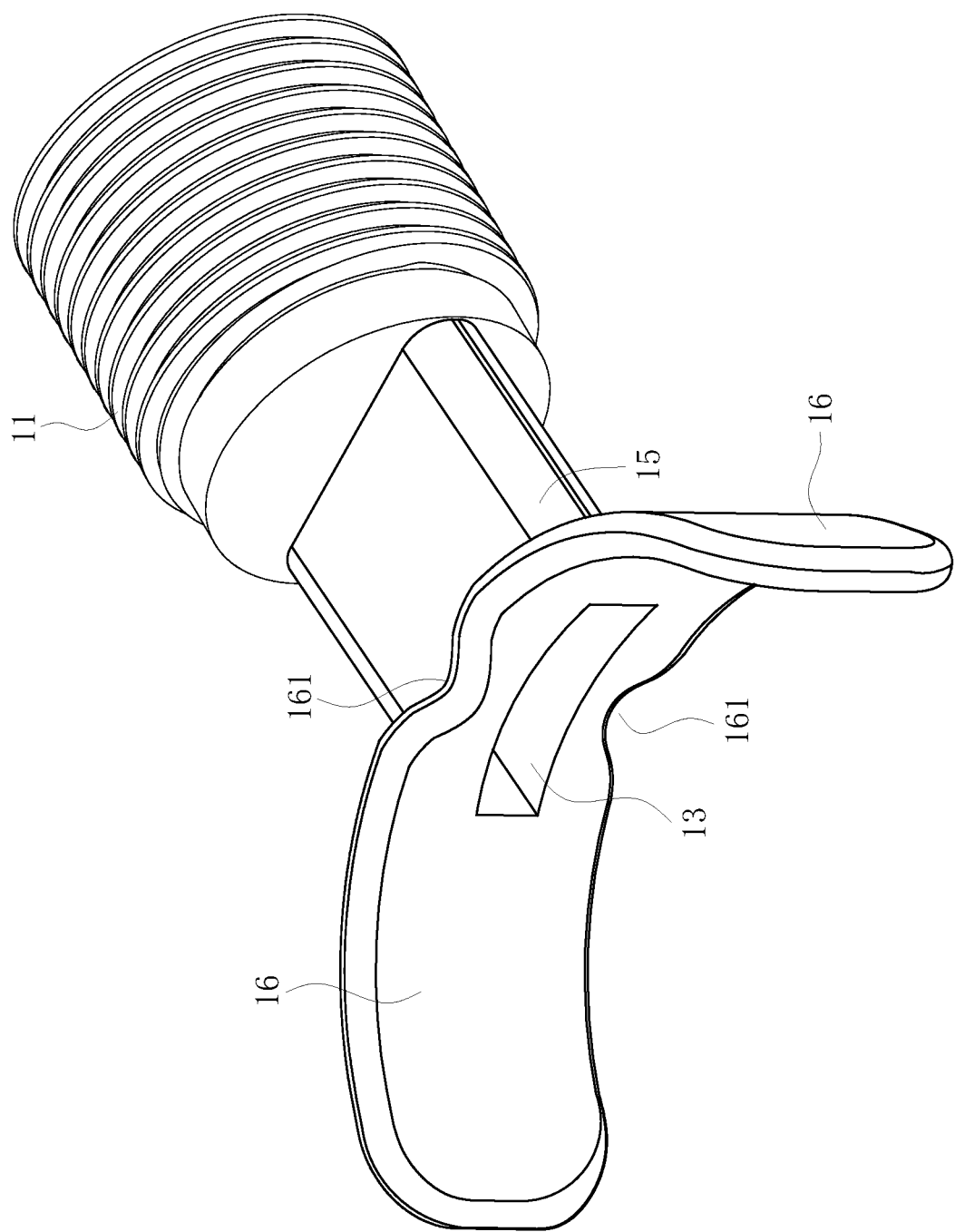
FIG. 10 is a perspective view of a base of FIG. 9.

Referring to FIG. 9 and FIG. 10, the base 10 in the second embodiment also has a cylindrical portion 11 which has the same structure and function as the cylindrical portion 11 in the first embodiment. In the second embodiment, the base 10 further has a flat portion 15 connected to the rear end of the cylindrical portion 11 and an inner expansion portion 16 connected to the rear end of the flat portion 15. The passage 13 penetrates the cylindrical portion 11 in the front-rear direction, the flat portion 15 and the inner expansion portion 16. The flat portion 15 is adapted to lie between the user's upper lip L and lower lip L when the device is in use; thus, the vertical dimension of the flat portion 15 is less than its transverse dimension in order for the flat portion 15 to match the user's lips L in terms of outline. To match the flat portion 15 in terms of outline, the channel 21 and the passage 13 penetrating the flat portion 15 have lesser vertical dimensions than their transverse dimensions. The inner expansion portion 16 is adapted to lie between the user's teeth D and lips L when the device is in use; thus, with the inner expansion portion 16 being fitted within the gap between the user's teeth D and lips L, the base 10 can be fixed to the user's head. To match the oral cavity structure between the user's teeth D and lips L in terms of outline, the inner expansion portion 16 bends and extends along the outer sides of the user's teeth D so as to become substantially U-shaped, whereas the inner expansion portion 16 extends upward and downward relative to the flat portion 15 to thereby be inserted into a gap between the user's gingiva and lips L. Two depressions 161 are disposed at the upper edge and lower edge of the inner expansion portion 16, respectively. The depressions 161 match a user's labial frenulum in terms of outline. In another embodiment, the inner expansion portion 16 is not required.

Referring to FIG. 9, a separable mechanism 83 provided in the second embodiment substitutes for the flexible portion 81 of the first embodiment. The separable mechanism 83 is tubular and is adapted to connect two disconnected parts of the connection pipe 80. The two ends of the separable mechanism 83 fit within the connection pipe 80. Under both of the two following conditions, namely the connection pipe 80 being stretched tight because the user has changed his/her sleeping position, and the connection pipe 80 having tension greater than a connecting force between the connection pipe 80 and the separable mechanism 83, the connection pipe 80 and the separable mechanism 83 are disconnected from each other, thereby preventing the taut connection pipe 80 from pulling the user's tongue T excessively.

Figure 11:
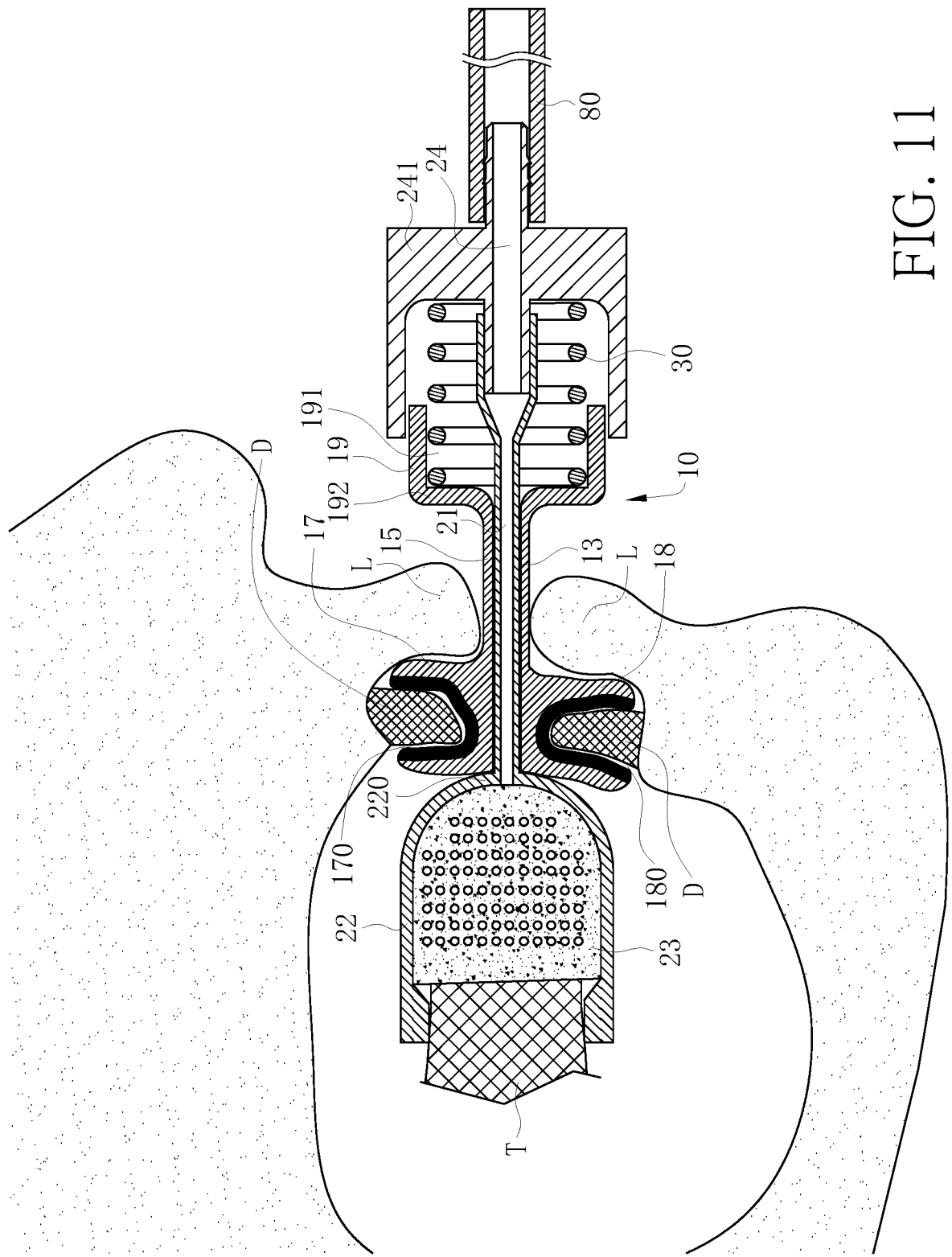
FIG. 11 is a schematic view of the device for alleviating obstructive sleep apnea according to the third embodiment of the present disclosure.

Referring to FIG. 11, the device for alleviating obstructive sleep apnea is provided according to the third embodiment of the present disclosure. In the third embodiment, the base 10 must enter the user's oral cavity in order for the device to work. The base 10 has an upper dental sheath 17 and a lower dental sheath 18 which are behind the flat portion 15. The passage 13 is disposed between the upper dental sheath 17 and the lower dental sheath 18. The upper dental sheath 17 has a receiving slot 170 for receiving the user's upper teeth D, and the lower dental sheath 18 has a receiving slot 180 for receiving the user's lower teeth D. Therefore, the base 10 can be fixed to the user's head with the upper dental sheath 17 and the lower dental sheath 18 being fitted to user's teeth D. In this embodiment, to render the device comfortable, the inner surfaces of the receiving slots 170, 180 are covered with a soft material (such as silicone) which is softer than the upper dental sheath 17 and the lower dental sheath 18 and is adapted to come into contact with the user's teeth D. The user's teeth D are surrounded by the upper dental sheath 17 when the device is in use, and thus the second stopping portion 220 abuts against at least one of the upper dental sheath 17 and the lower dental sheath 18 rather than directly abutting against the user's teeth D. In this embodiment, the second stopping portion 220 abuts against the upper dental sheath 17 and the lower dental sheath 18.

Referring to FIG. 11, in this embodiment, the upper dental sheath 17 and the lower dental sheath 18 are substantially vertically aligned with each other and thus are available for use by general users. In another embodiment, to treat users with severe obstructive sleep apnea, the lower dental sheath 18 is adapted to protrude forward relative to the upper dental sheath 17 and thus pull the user's lower jaw forward, such that the user's tongue T attached to the lower jaw undergoes forward displacement to thereby stay away from the user's throat.

Referring to FIG. 11, in this embodiment, the device does not have either adjustment element 40. The base 10 has an enlarged portion 19 located outside the user's lips L. The enlarged portion 19 surrounds the channel 21 such that an annular cavity 191 is formed therebetween. The annular cavity 191 forwardly penetrates the base 10. The enlarged portion 19 has a stopping surface 192 positioned proximate to the rear end of the annular cavity 191. The connector 24 in this embodiment is structurally similar to the integrally-formed structure of the connector 24 and second adjustment element 40b in the first embodiment. The connector 24 is also tubular. A protrusion portion 241 is disposed at the middle of the connector 24 and protrudes radially therefrom. The outer edge of the protrusion portion 241 extends rearward and thus partially covers the enlarged portion 19 and the resilient element 30. The resilient element 30 is contained in the annular cavity 191 and the protrusion portion 241 and fitted around the channel 21. The rear end of the resilient element 30 rearwardly abuts against the stopping surface 192. The front end of the resilient element 30 directly abuts against the rear end of the protrusion portion 241.

Referring to FIG. 12 through FIG. 15, the device for alleviating obstructive sleep apnea is provided according to the fourth embodiment of the present disclosure. The device comprises a base 10 connected to the user's head, a suction member 20 for pulling the user's tongue (not shown) forward, a resilient element 30, a first adjustment element 40a for adjusting the forward displacement of the user's tongue, and a negative pressure source (not shown).

Figure 13:
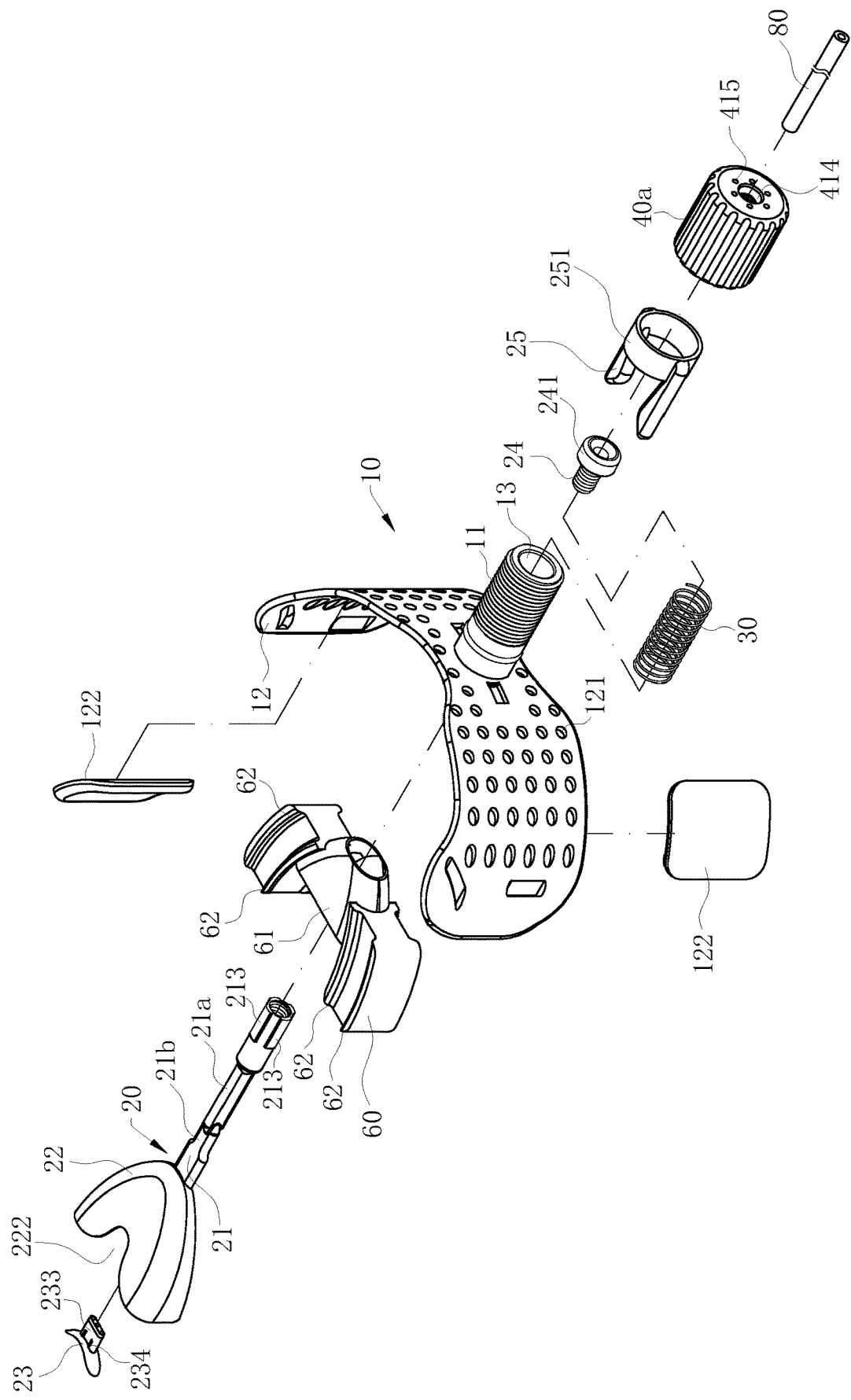
FIG. 13 is an exploded view based on FIG. 12.
Figure 14:
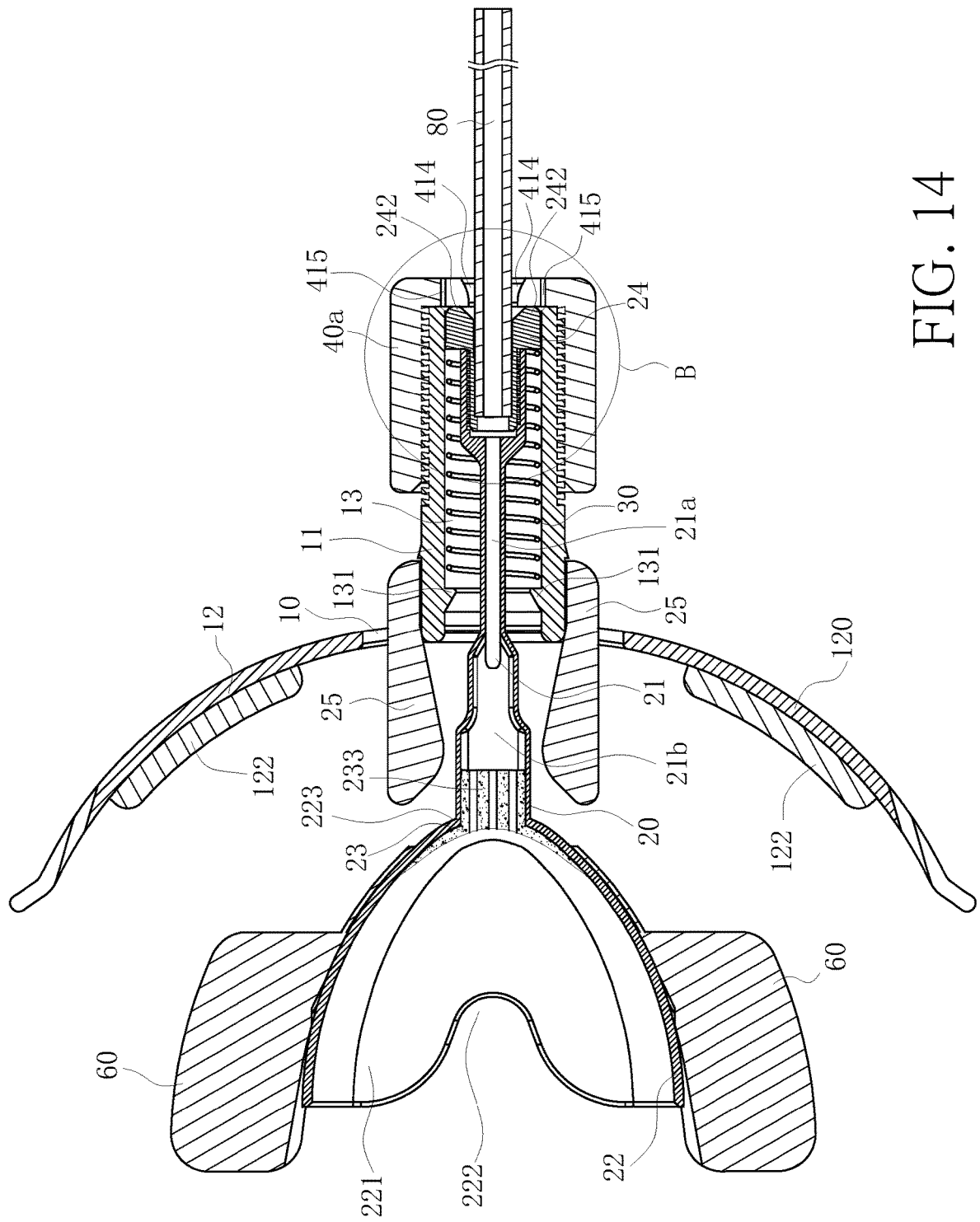
FIG. 14 is a cross-sectional view based on FIG. 12.

Referring to FIG. 13 and FIG. 14, the first and fourth embodiments are similar in terms of the general structure of the suction member 20; thus, the similar structure will not be described in detail herein. Referring to FIG. 14, in the fourth embodiment, the outer diameter of the channel 21 is significantly less than the diameter of the passage 13 such that the channel 21 does not fill the passage 13 completely. Thus, a gap exists between the channel 21 and the base 10, thereby creating room for the vertical or transverse movement of the suction member 20.

Referring to FIG. 13, the channel 21 comprises a front segment 21a and a rear segment 21b disposed behind the front segment 21a. The vertical dimension of the front segment 21a is greater than its transverse dimension and thus the front segment 21a is uprightly cord-shaped to increase the bendability of the channel 21 in the transverse direction. The vertical dimension of the rear segment 21b is less than its transverse dimension and thus the rear segment 21b is horizontally cord-shaped to increase the bendability of the channel 21 in the vertical dimension. The channel 21 bends and deforms relative to the transverse direction as soon as the front segment 21a bends and deforms relative to the transverse direction. The channel 21 bends and deforms relative to the vertical direction as soon as the rear segment 21b bends and deforms relative to the vertical direction. Therefore, the difference in shape between the front segment 21a and the rear segment 21b of the channel 21 confers their deformability relative to the transverse direction and relative to the vertical dimension, respectively. Conversely, when the channel 21 bends relative to the transverse direction, its transverse deformation is concentrated in the front segment 21a. When the channel 21 bends relative to the vertical direction, its vertical deformation is concentrated in the rear segment 21b. The tongue fixing portion 22 is connected to the rear end of the channel 21 and thus is connected to the rear segment 21b. Therefore, the tongue fixing portion 22 can move in a direction perpendicular to the front-rear direction and in directions other than perpendicular to the front-rear direction; i.e., it can move upward, downward, leftward and rightward because of the bending and deformation of the channel 21 so as to ensure the flexibility of movement of the tongue fixing portion 22 and the user's tongue. In another embodiment, the vertical dimension of the front segment 21a is less than its transverse dimension and thus the front segment 21a is horizontally cord-shaped, whereas the vertical dimension of the rear segment 21b is greater than its transverse dimension and thus the rear segment 21b is uprightly cord-shaped, thereby allowing the tongue fixing portion 22 to move in directions perpendicular to the front-rear direction and in directions other than perpendicular to the front-rear direction.

Figure 15:
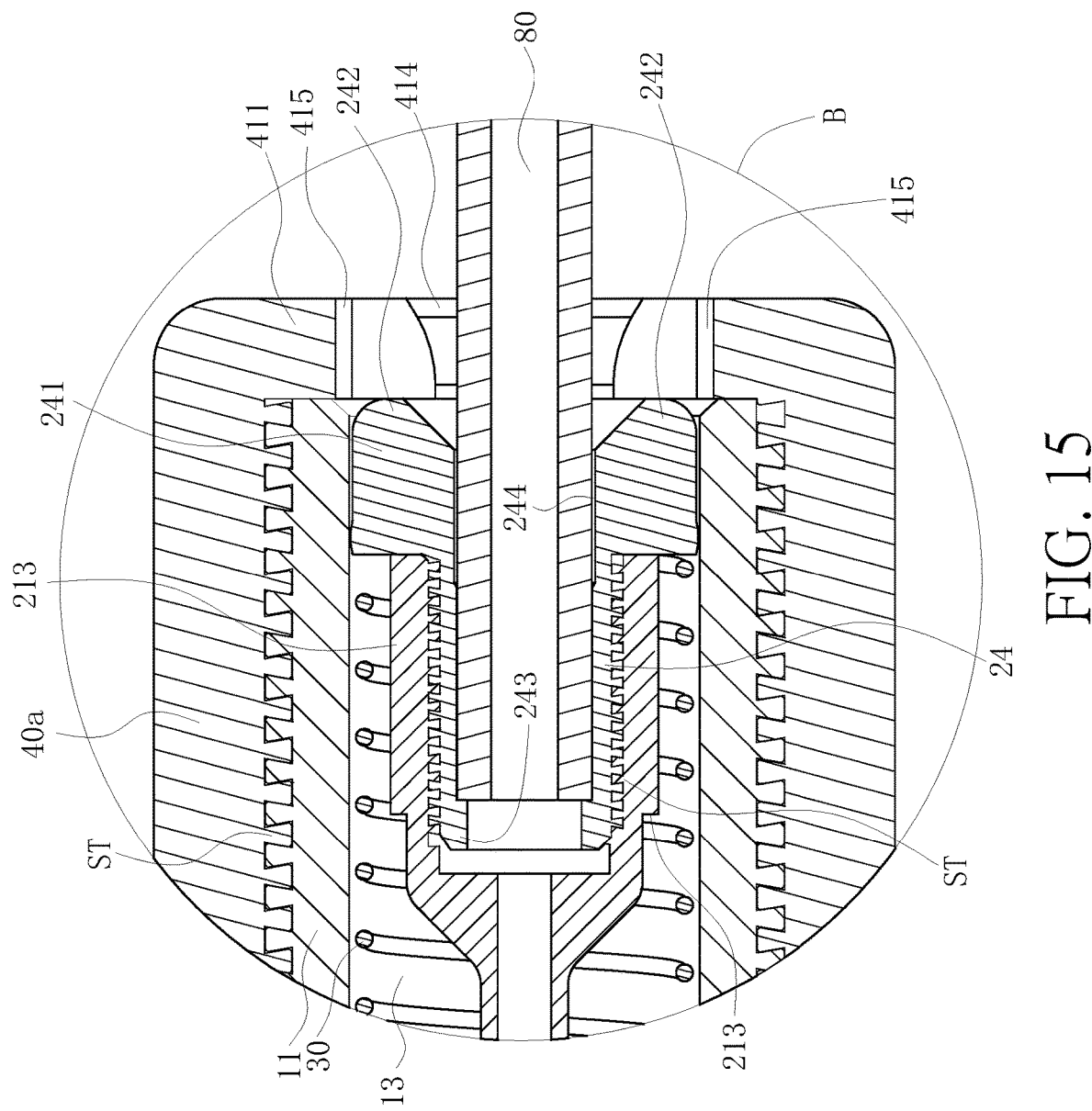
FIG. 15 is an enlarged view of part B in FIG. 14.

Referring to FIG. 14 and FIG. 15, in this embodiment, the front end of the channel 21, i.e., the front of the front segment 21a, is cylindrical and receives the connector 24. The channel 21 and the connector 24 are connected by threads. The front end of the connector 24 extends beyond the channel 21 to form the protrusion portion 241, which radially protrudes relative to the connector 24 received in the channel 21. The front end of the protrusion portion 241 functions as a stopping portion, which is defined as a third stopping portion 242. The third stopping portion 242 and the first adjustment element 40a abut against each other. The connector 24 receives and fixes the connection pipe 80 in place. A step portion 243 is disposed in the rear end of the connector 24. The step portion 243 protrudes from the wall of the connector 24 and can abut against the connection pipe 80 to prevent the connection pipe 80 from passing through the connector 24. A binder receiving portion 244 is disposed at the front end of the connector 24 and in the protrusion portion 241. The diameter of the binder receiving portion 244 is greater than the outer diameter of the connection pipe 80 such that the binder receiving portion 244 can receive a specific amount of binder, thereby further fixing the connector 24 and the connection pipe 80 to each other. In another embodiment, the outer diameter of the connection pipe 80 is greater than the diameter of the connector 24 such that the connection pipe 80 and the connector 24 are interferingly fixed together by interfering connection, thereby enabling the binder receiving portion 244 to guide the process of connecting the connection pipe 80 and the connector 24.

Referring to FIG. 14 and FIG. 15, the connector 24 comprises a fitting portion 245 which connects the connector 24 to the channel 21 by a thread. The fitting portion 245 in this embodiment is received in the channel 21. In another embodiment, the fitting portion 245 receives the channel 21. The fitting portion 245 fits around the connection pipe 80. A sliding portion 246 is defined on the radial outer side of the protrusion portion 241. The surface of the sliding portion 246 is smoothened to reduce the friction otherwise generated as a result of the contact between the sliding portion 246 and the inner wall of the cylindrical portion 11.

Referring to FIG. 13 and FIG. 14, the protective pad 23 has a fixing protruding portion 233 protruding forward. The fixing protruding portion 233 passes through the air inlets 223 to enter the rear segment 21b. The fixing protruding portion 233 matches the rear segment 21b in shape. The upper and lower surfaces of the fixing protruding portion 233 each have two interference portions 234 for augmenting the gripping force between the fixing protruding portion 233 and the rear segment 21b. In the fourth embodiment, the interference portions 234 are provided in the form of raised ridges extending in the front-rear direction but may be replaced by raised dots or the like. In another embodiment, the raised interference portions 234 are disposed on the inner surface of the wall of the rear segment 21b, whereas the surface of the fixing protruding portion 233 may even have indentations which match the interference portions 234 in shape to fix the fixing protruding portion 233 and the rear segment 21b to each other more firmly.

Figure 12:
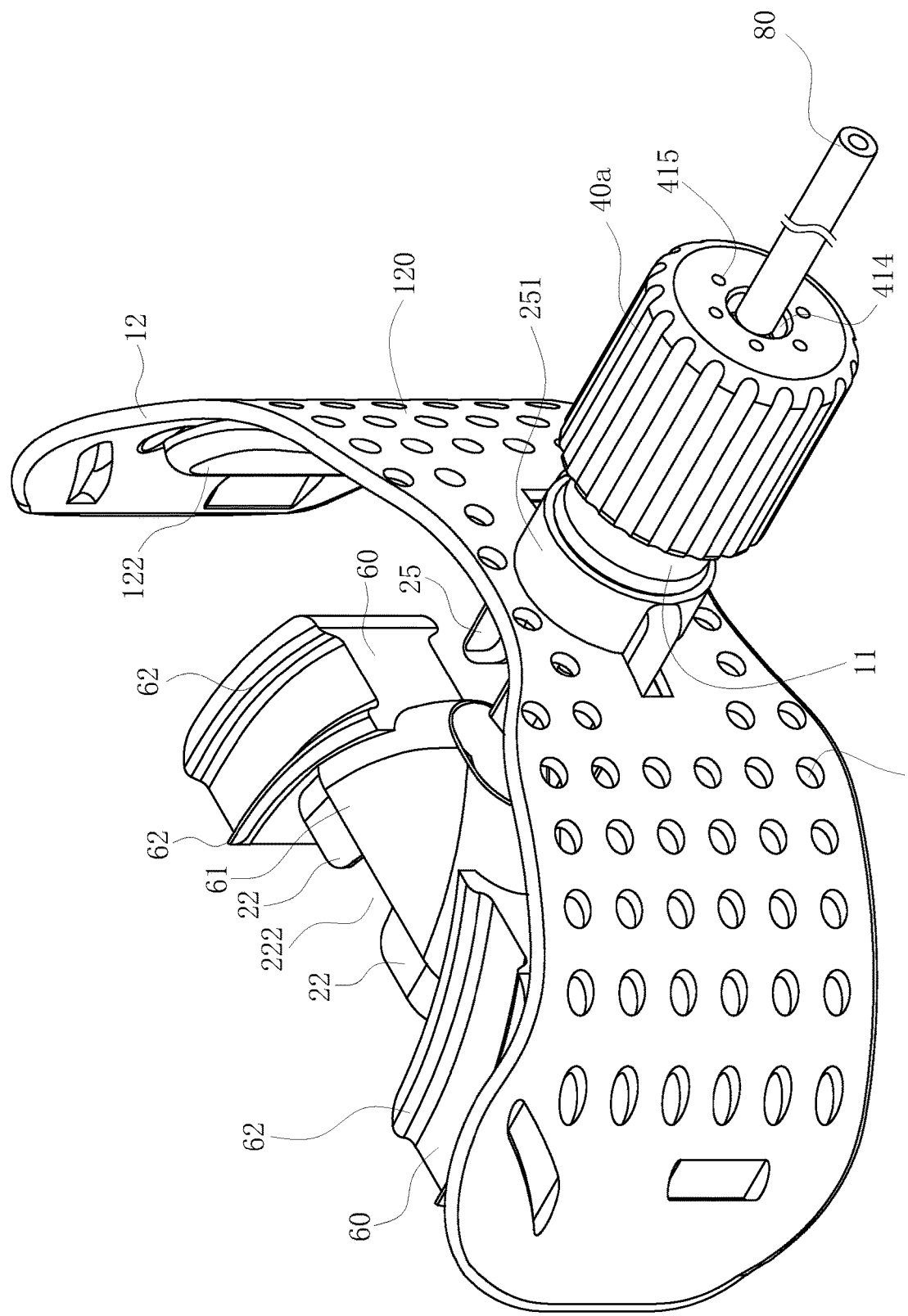
FIG. 12 is a schematic view of the device for alleviating obstructive sleep apnea according to the fourth embodiment of the present disclosure.

Referring to FIG. 12 through FIG. 14, the base 10 in the fourth embodiment is substantially the same as the base 10 in the first embodiment except that, in the fourth embodiment, the inner side of the main body 120 of the outer expansion portion 12 has two pads 122 which face the user's face. The pads 122 are made of an air-permeable material, such as sponge, thereby having two advantages: the outer expansion portion 12 attached to the user's face is comfortable, and air can still permeate the material to reach the user's facial skin compressed by the outer expansion portion 12. The passage 13 contains the front segment 21a, the resilient element 30 and the connector 24 simultaneously. Therefore, the cylindrical portion 11 and the passage 13 in the fourth embodiment are longer than their counterparts in the first embodiment.

Referring to FIG. 14, the resilient element 30 fits around the front segment 21a, with its front end abutting against the protrusion portion 241 from behind and its rear end abutting against a stopping element 131 in the passage 13. In this embodiment, the stopping element 131 and the base 10 are integrally formed. Therefore, in this embodiment, the elastic force of the resilient element 30 directly acts on the base 10 and the suction member 20. In another embodiment, the resilient element 30 is fixed to the base 10 and the suction member 20 with rivets, pins, or binders. In this embodiment, the spring-style resilient element 30 is closer to the inner wall surface of the passage 13 than is the channel 21 to prevent the resilient element 30 from interfering with the channel 21 as a result of non-axial deformation.

Referring to FIG. 13 and FIG. 14, in this embodiment, a protecting member 25 is demountably disposed on the base 10. The protecting member 25 comprises a ring 251. The ring 251 fits around the cylindrical portion 11. The protecting member 25 extends rearward and passes through the outer expansion portion 12 and is disposed on the left and right sides of the rear segment 21b. The protecting member 25 is of a greater thickness than the rear segment 21b to prevent the user's teeth D from directly biting the channel 21 and thus damaging the channel 21.

Referring to FIG. 12 through FIG. 14, in the fourth embodiment, the first adjustment element 40a, which is cylindrical and sleeve-shaped, fits around the cylindrical portion 11 to enable the first adjustment element 40a and the cylindrical portion 11 to be connected by threads, thereby allowing the user to move the first adjustment element 40a along the cylindrical portion 11 by rotating the first adjustment element 40a. Grooves and ridges extending in the front-rear direction of the first adjustment element 40a are disposed on the outer circumferential surface of the first adjustment element 40a to increase its friction. A plurality of communication holes 415 surrounding the penetrating hole 414 are disposed in the baffle 411 of the first adjustment element 40a. The penetrating hole 414 and communication holes 415 are all in communication with the passage 13. The penetrating hole 414 has a diameter which increases toward the front end of the penetrating hole 414 to thereby provide a certain degree of room for the swinging of the connection pipe 80 passing through the penetrating hole 414. The communication holes 415 release gas or liquid previously admitted into the passage 13. The front end of the first adjustment element 40a functions as the baffle 411, such that it and the third stopping portion 242 abut against each other. By moving the first adjustment element 40a forward and rearward, the user changes the position at which the first adjustment element 40a and the third stopping portion 242 abut against each other, so as to adjust the position of the suction member 20 and the position of the user's tongue. Specifically, the user forwardly moves the first adjustment element 40a, and the compression spring functioning as the resilient element 30 is loosened to thereby forwardly stretch and push the connector 24 and thus drive the suction member 20 to move forward; meanwhile, the user's tongue moves forward together with the suction member 20 until the third stopping portion 242 abuts against the baffle 411 once again. Conversely, if the user moves the first adjustment element 40a rearward, the forward displacement of the user's tongue will decrease.

In this embodiment, the predetermined position of the tongue fixing portion 22 in operation requires the tongue fixing portion 22 to be disposed behind the user's teeth D. However, the predetermined position is unlikely to preclude the collapse of the tongue otherwise typical of users with severe obstructive sleep apnea. Treatment for these users entails moving the first adjustment element 40a forward to augment the forward displacement of the tongue. In general, when the front end of the user's tongue protrudes forward beyond the user's teeth D, treatment for these users is satisfactory. To prevent the protecting member 25 from impeding the forward movement of the tongue fixing portion 22, adjustment is preceded by removal of the protecting member 25. Furthermore, these users must use the occlusion portion 60 in order to prevent the user's teeth D from biting the tongue fixing portion 22.

Referring to FIG. 12 through FIG. 14, in this embodiment, the device comprises two occlusion portions 60. The two occlusion portions 60 are connected by a connection portion 61. The connection portion 61 fits around the tongue fixing portion 22. Two limiting ribs 62 are disposed at each occlusion portion 60 and face the upper edge and lower edger of the user's teeth D, respectively. When the device is in use, the two limiting ribs 62 are positioned on the inner side and outer side of the user's teeth D, respectively, thereby confining the occlusion portion 60 to the space between the user's upper teeth D and lower teeth D.

Most parts and components of the device, including the adjustment element 40, the base 10, the connector 24 and the channel 21, are made of soft materials. If the threads of the parts and components are integrally formed and made of soft materials, conventional profile of threads, such as triangular thread and trapezoidal thread, cannot provide sufficient bonding strength, so conventional threads will undergo tooth deformation, subsequent slippage, and ultimate separation of the two threads. Referring to FIG. 15, to solve this issue, the threads between the first adjustment element 40a and the base 10 as well as the threads between the fitting portion 245 and the channel 21 are threads ST with a special profile of thread. The profile of thread of threads ST is characterized in that the width of the crest is greater than the width of the root in the axial direction of the threads. In this embodiment, the thread ST is dovetail-shaped or, in other words, inverted-trapezoidal, as opposed to the conventional trapezoidal shape. The features of the dovetail-shaped or inverted-trapezoidal thread ST are as follows: in the axial direction of the thread, the width of each thread increases gradually from the root toward the crest; each crest of the external thread overlaps a corresponding crest of the internal thread in the radial direction, such that each crest of the external thread and a corresponding crest of the internal thread limit the movement of each other in the radial direction so as to prevent separation of a crest from a corresponding root. Therefore, the slippage and separation of two threads made of a soft material is impossible. However, the shape of the teeth of the thread ST is not restricted to the abovementioned shapes and thus, for example, the teeth of the thread ST can be T-shaped.

Both the soft channel 21 and the soft connector 24 are fitted together by using an automated mechanical apparatus (not shown). In this embodiment, the channel 21 fits to the connector 24 from the outside. Referring to FIG. 13 and FIG. 15, a plurality of bumps 213 each radially protrude from the outer surface of the front end of the channel 21 and extend in the front-rear direction to operate in conjunction with a mechanical apparatus (not shown) so as to not only enable the mechanical apparatus (not shown) to position the channel 21 in place but also fix the channel 21 in place when the channel 21 and the connector 24 are fitted together. In the embodiment where the channel 21 fits within the connector 24, the bumps 213 are disposed on the outer surface of the connector 24.

Figure 16:
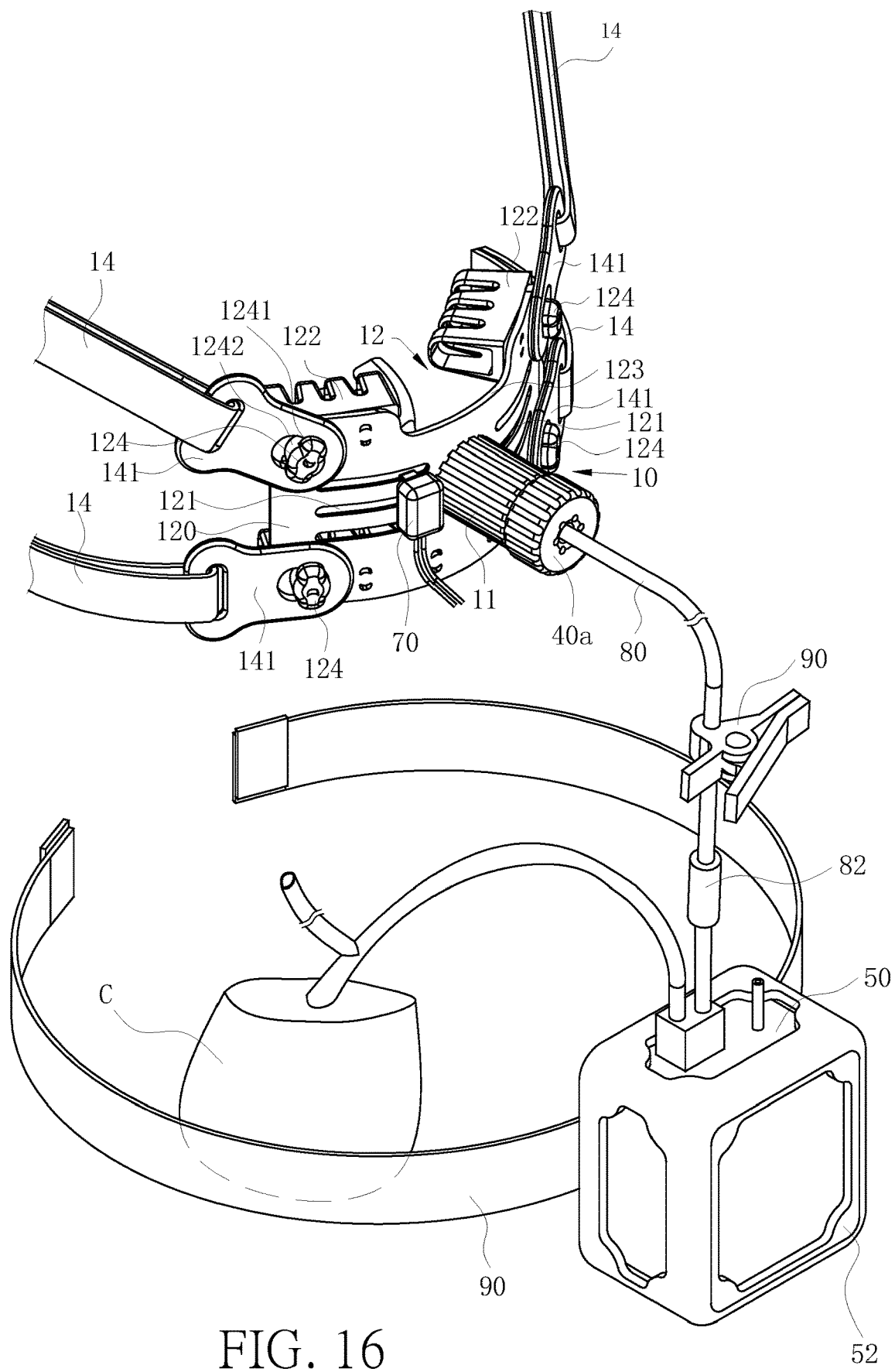
FIG. 16 is a schematic view of the device for alleviating obstructive sleep apnea according to the fifth embodiment of the present disclosure.

Referring to FIG. 16, the device for alleviating obstructive sleep apnea is provided according to the fifth embodiment of the present disclosure. The device for alleviating obstructive sleep apnea comprises a base 10 fitted and fixed to the user's head, a suction member 20 for applying suction to the user's tongue (not shown), a driving mechanism joined to the base 10 and the suction member 20, a first adjustment element 40a for adjusting the forward displacement of the user's tongue, and a negative pressure source 50 whereby the suction member 20 is provided with a negative pressure to apply suction to the user's tongue. The driving mechanism is a resilient element 30, such as a spring. A breath sensor 70 is mounted on the base 10. The negative pressure source 50, the connection pipe 80 and the fixing mechanisms 90 in this embodiment are identical to their counterparts in the first embodiment and thus are, for the sake of brevity, not described again.

Figure 17:
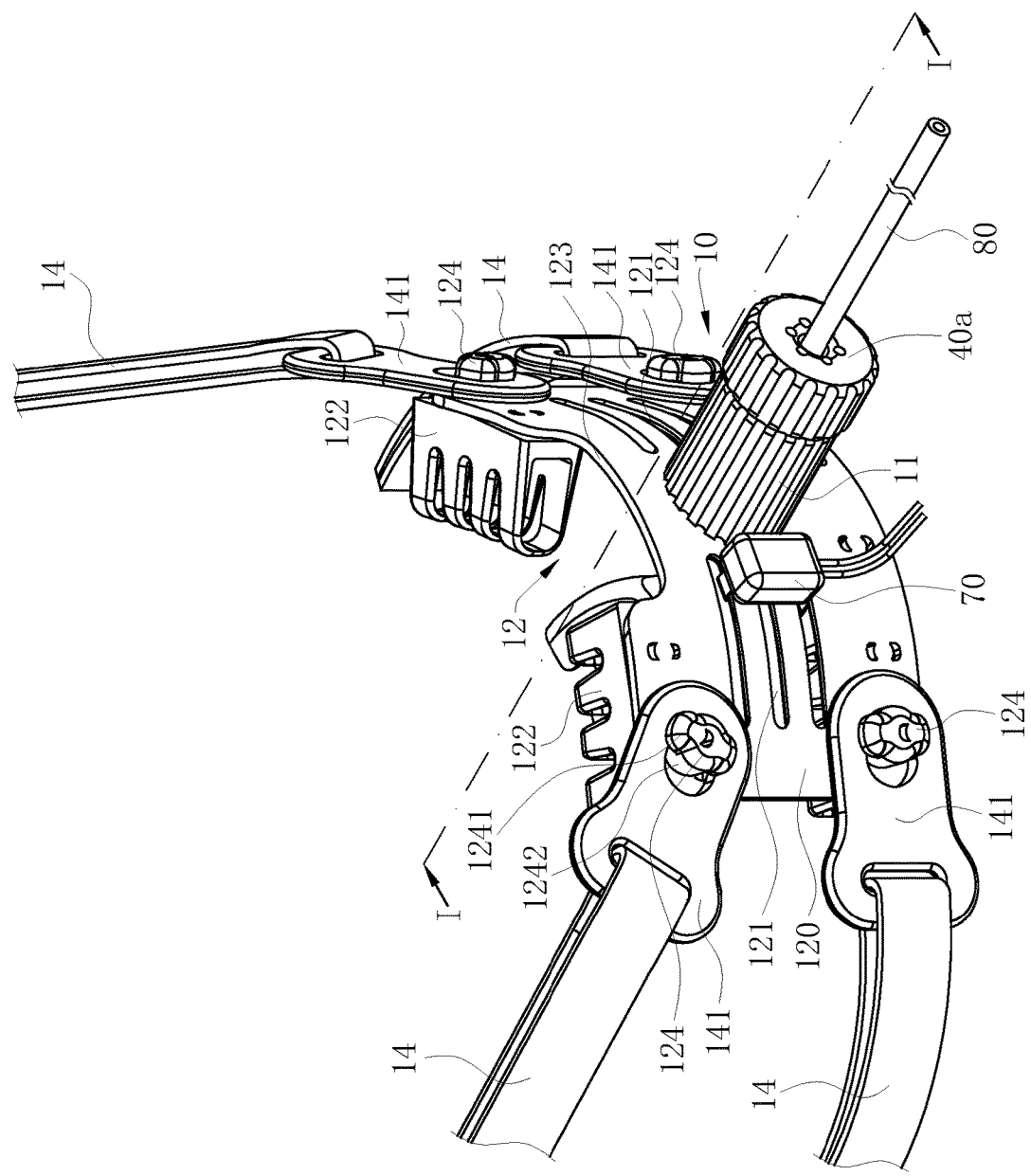
FIG. 17 is an enlarged view based on FIG. 16 with the negative pressure source not shown.
Figure 20:
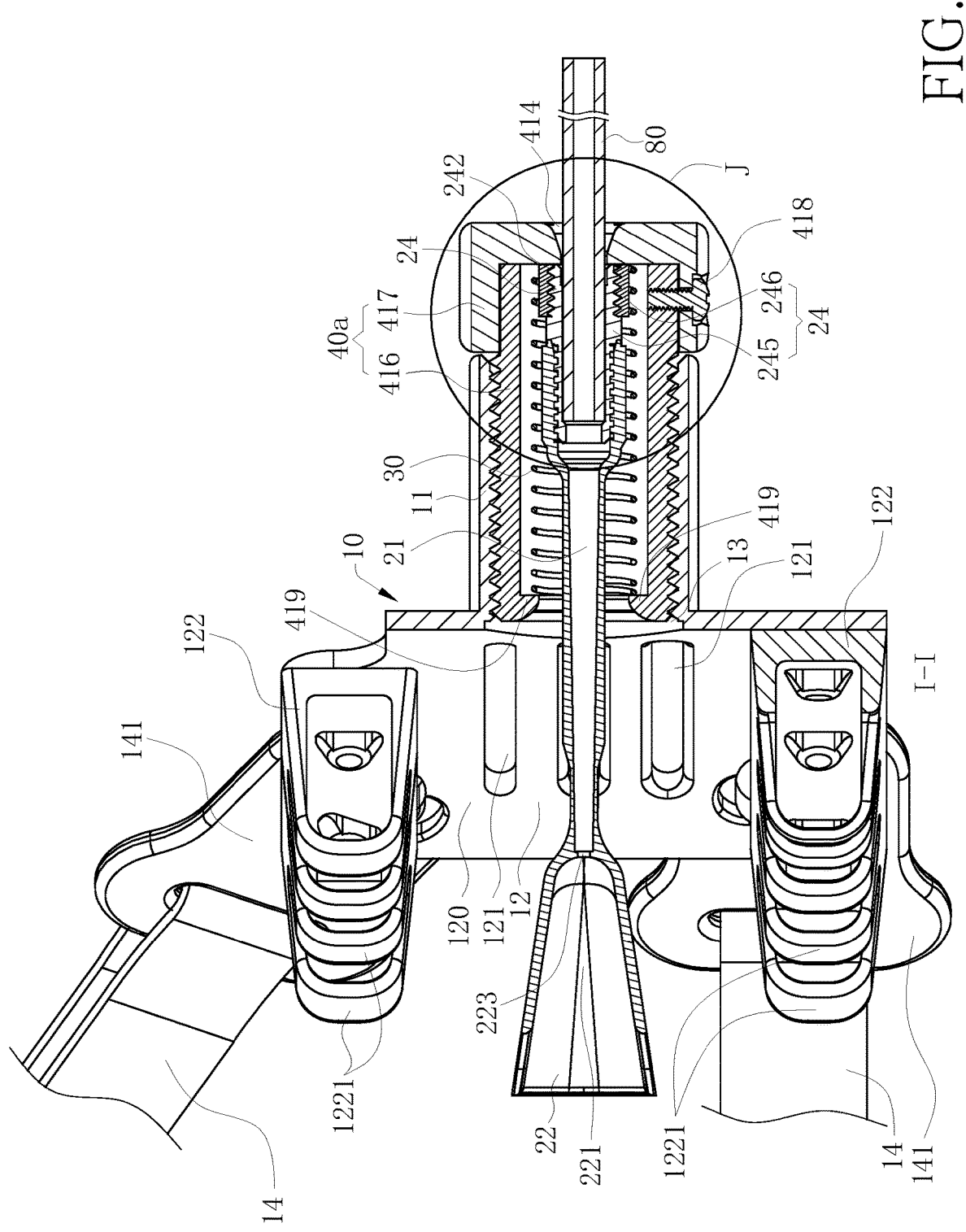
FIG. 20 is a cross-sectional view taken along line I-I of FIG. 17.

Referring to FIG. 17 and FIG. 20, the base 10 has a cylindrical portion 11, an outer expansion portion 12 connected to the cylindrical portion 11 from behind, and a passage 13 penetrating the cylindrical portion 11 at the front and the outer expansion portion 12 at the rear, thereby allowing the cylindrical portion 11 to protrude forward relative to the outer expansion portion 12. In this embodiment, the main body 120 of the outer expansion portion 12 has a plurality of perforations 121 which are parallel, horizontal and slender. The perforations 121 penetrates an outer surface of the outer expansion portion 12, which is the surface away from the user's face, and penetrates an inner surface of the outer expansion portion 12, which the surface facing the user's face. The breath sensor 70 is fixed to the outer expansion portion 12 through the perforations 121.

Figure 18:
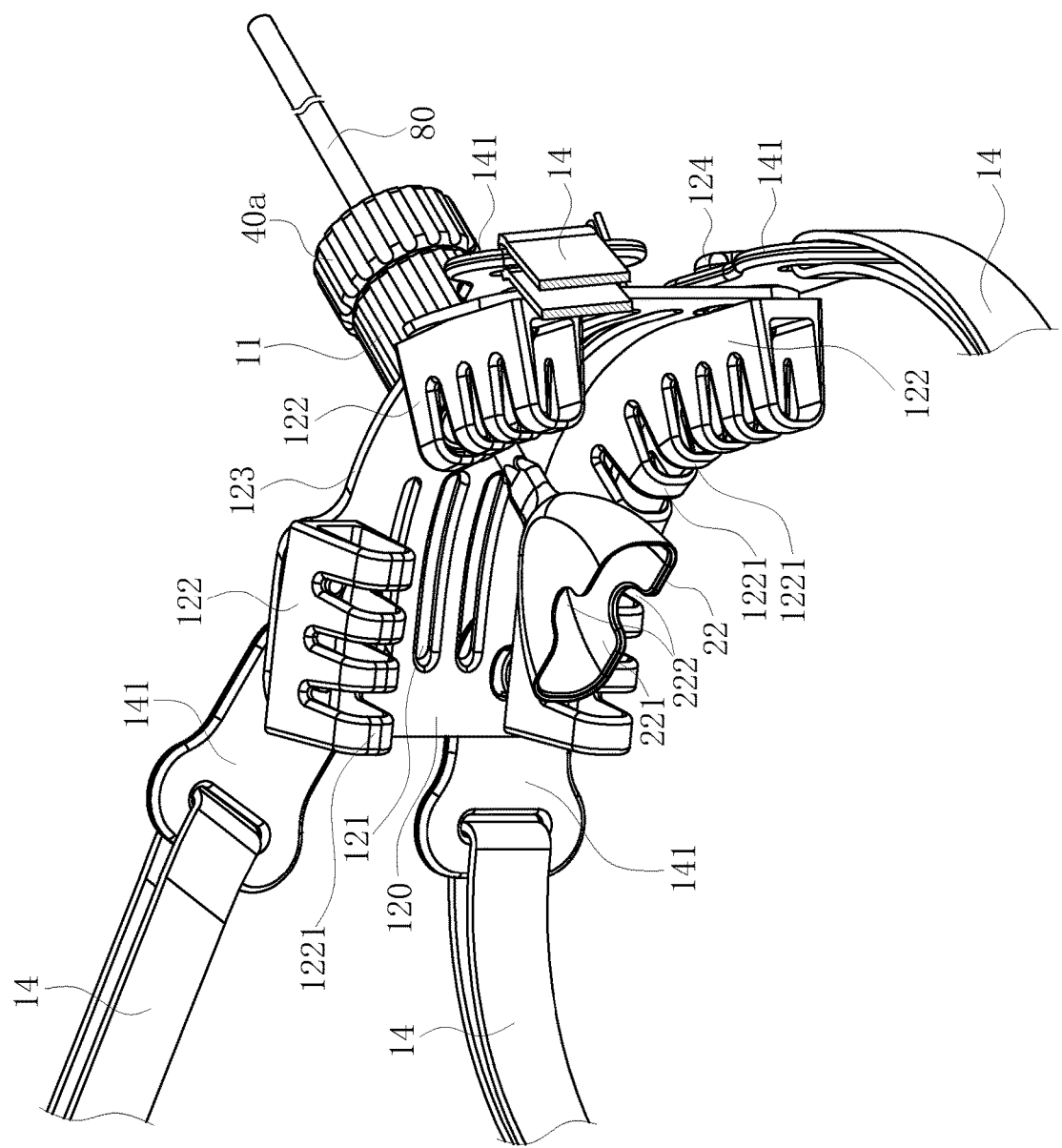
FIG. 18 is a schematic view of FIG. 17 rotated 90 degrees counterclockwise.

Referring to FIG. 17 and FIG. 18, the outer expansion portion 12 in this embodiment is of a smaller size than its counterparts in the preceding embodiments. The outer expansion portion 12 is located outside the user's oral cavity and have a size greater than the mouth, but only covers the user's lips and the immediate vicinity thereof. The pads 122 are fixed to the inner side of the main body 120 of the outer expansion portion 12 and thus face the user's face, wherein the pads 122 are elastically stretched and contracted relative to the main body 120. A wide cut 123 is formed on the upper edge of the main body 120 of the outer expansion portion 12. The wide cut 123 matches the user's nose in terms of outline to make way for the user's nose. The two pads 122 are disposed on the left and right sides of the wide cut 123, respectively, such that they come into contact with the facial skin above the user's upper lip. The other pad 122 is disposed at the lower end of the main body 120 of the outer expansion portion 12 and such that it comes into contact with the facial skin under the user's lower lip.

Figure 19:
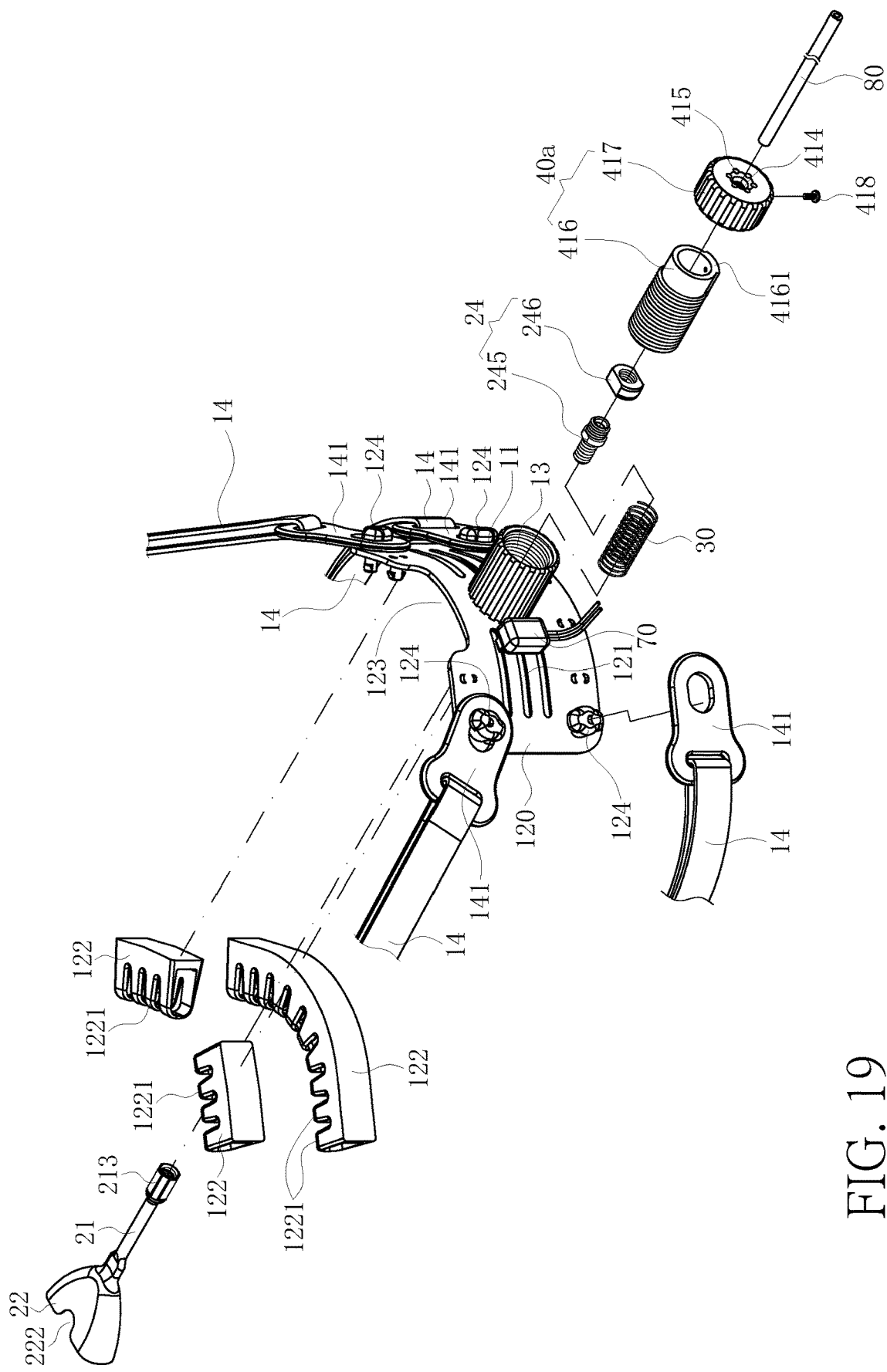
FIG. 19 is an exploded view based on FIG. 17.

Referring to FIG. 18 and FIG. 19, each pad 122 comprises a plurality of finger portions 1221 protruding toward the user's face. The finger portions 1221 are each penetrated by a hollow-cored portion in a direction joining the finger portions 1221. Owing to their softness and the hollow-cored portions, the finger portions 1221 deform after coming into contact with the user's face. The deformation requires the terminal ends of the finger portions 1221 to contract toward the outer expansion portion 12 and the upper and lower sides of the finger portions 1221 to expand and thus enables absorption of the pressure imposed by the outer expansion portion 12 on the user's face. The finger portions 1221 at the same pad 122 are spaced apart. The transverse width of each finger portion 1221 decreases gradually in the direction from the main body 120 toward the user's face, whereas the transverse distance between two adjacent said finger portions 1221 increases gradually, thereby allowing the finger portions 1221 to match the outer expansion portion 12 and the user's face in terms of curvature. Referring to FIG. 17 and FIG. 18, four block portions 124 are disposed at the four corners on the outer side of the outer expansion portion 12, respectively. The block portions 124 protrude from the outer surface of the main body 120 of the outer expansion portion 12. The block portions 124 each comprise a crown portion 1241 and a stalk portion 1242. The stalk portion 1242 is connected to the outer surface of the main body 120 of the outer expansion portion 12. The crown portion 1241 protrudes relative to the stalk portion 1242. A slot (not shown) is formed between the crown portion 1241 and the outer surface of the outer expansion portion 12, and the corresponding fixing element 14 is anchored to the slot. Each fixing element 14 has a buckle 141 engageable with the corresponding stalk portion 1242 and rotatable about the stalk portion 1242. The crown portion 1241 and the buckle 141 abut against each other to prevent separation of the fixing element 14 from the outer expansion portion 12.

For most users, there is a distance between the position of the collapsed tongue and the farthest possible position of the pulled tongue, and obstructive sleep apnea can be alleviated if the tongue is not at the tongue-collapsed position. However, the aforesaid distance varies from user to user to allow the users' tongues to be at comfortable positions. Therefore, the device comes with the first adjustment element 40a, whereby the users adjust the aforesaid distance, and the first adjustment element 40a is located outside the user's oral cavity.

Referring to FIG. 19 and FIG. 20, the cylindrical portion 11 protrudes forward from the outer surface of the outer expansion portion 12, and the passage 13 penetrates the cylindrical portion 11 at the front and the outer expansion portion 12 at the rear. In this embodiment, the cylindrical portion 11 has an internal thread directly exposed within the passage 13. The first adjustment element 40a comprises a cylindrical screw portion 416 covered with an external thread and received in the cylindrical portion 11. The external thread of the screw portion 416 meshes with the internal thread of the cylindrical portion 11. The front end of the screw portion 416 is covered with an operating cap 417. The operating cap 417 is fixed to the screw portion 416 by a screw 418. The circumferential surface of the operating cap 417 has parallel ridges, which extend in the front-rear direction to increase friction such that the user can easily rotate the operating cap 417 in order to rotate the entire first adjustment element 40a. To limit the depth by which the first adjustment element 40a can be inserted into the cylindrical portion 11, the diameter of the operating cap 417 is greater than the inner diameter of the cylindrical portion 11 such that the rear end of the operating cap 417 and the front end of the cylindrical portion 11 abut against each other.

Referring to FIG. 19 and FIG. 20, in the fifth embodiment, the screw 418 is inserted into the operating cap 417 and the screw portion 416 simultaneously to serve as a transmission mechanism whereby the operating cap 417 drives the rotation of the screw portion 416. The screw portion 416 has a part corresponding in position to the screw 418 and protruding radially to form a positioning protrusion 4161 which matches a positioning slot (not shown) of the operating cap 417 to thereby facilitate the alignment of pores disposed on the screw portion 416 and the operating cap 417 and adapted to receive the screw 418. Furthermore, the fourth and fifth embodiments have a technical feature in common; that is, the communication holes 414 and the communication holes 415 are disposed at the front end of the first adjustment element 40a. In the fifth embodiment, the penetrating hole 414 and the communication holes 415 are disposed at the operating cap 417.

Referring to FIG. 18 and FIG. 20, in the fifth embodiment, the channel 21 of the suction member 20 extends and passes through the passage 13 to enter the user's oral cavity and undergo displacement within the passage 13. The rear end of the of the channel 21 is connected to the tongue fixing portion 22, and the tongue fixing portion 22 is used to be disposed at the front end of the user's tongue. The front end of the channel 21 is connected to a connector 24.

Figure 21:
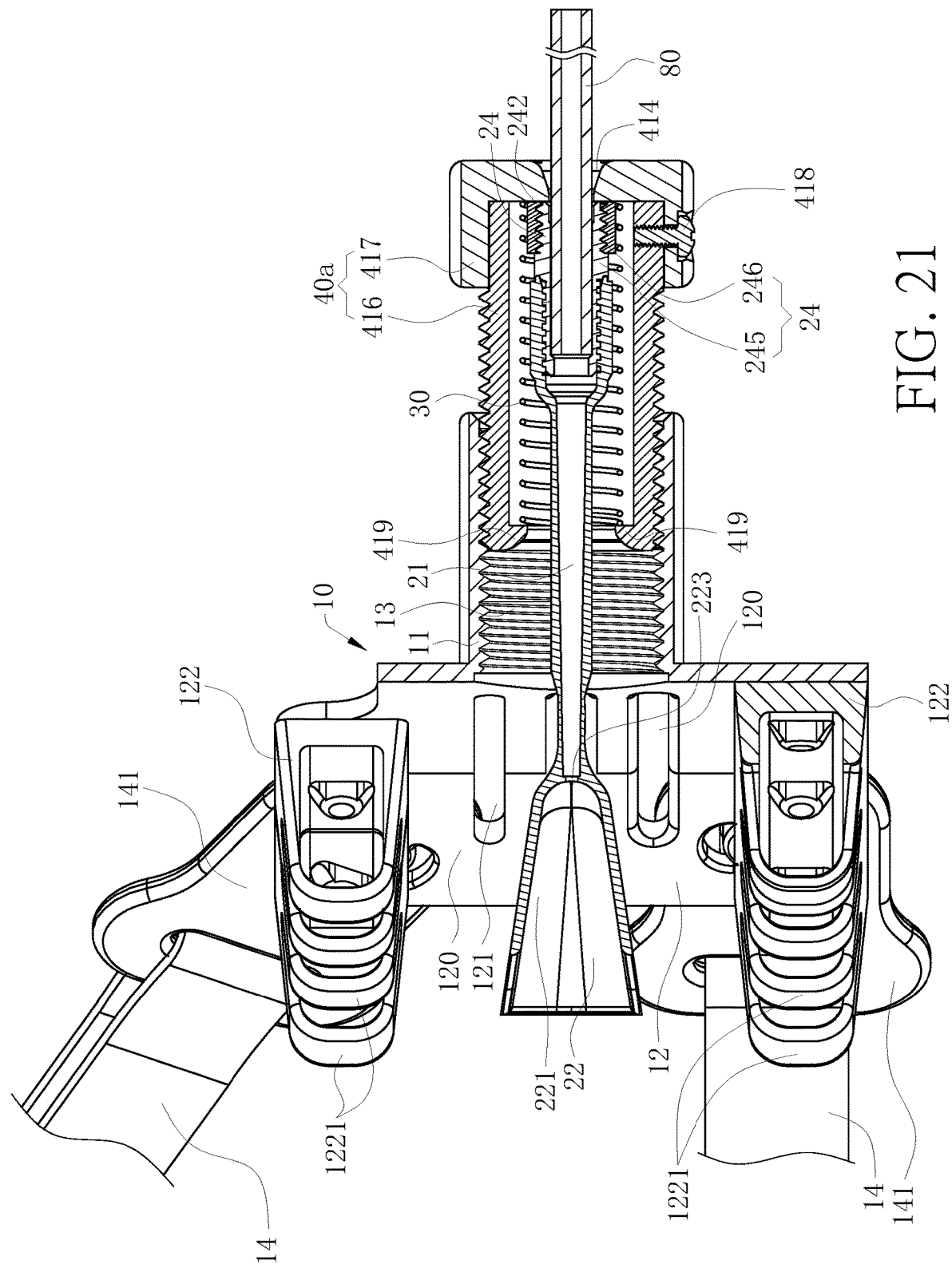
FIG. 21 is a schematic view of the forwardly-moved suction member and adjustment element in FIG. 20.

Referring to FIG. 19 and FIG. 20, in the fifth embodiment, the front end of the channel 21, the connector 24, the resilient element 30, and a portion of the connection pipe 80 are received in the first adjustment element 40a. The resilient element 30 fits around the channel 21, and at least part of the resilient element 30 is closer to the first adjustment element 40a than is the channel 21 within a rear part of the first adjustment element 40a, so as to prevent the resilient element 30 from interfering with the channel 21. In the fifth embodiment, a rear part of the resilient element 30 is closer to the first adjustment element 40a than is the channel 21. In another embodiment, the entire part of resilient element 30 may be closer to the first adjustment element 40a than is the channel 21. The connective relationship between the channel 21, the connector 24 and the connection pipe 80 of the fifth embodiment is the same as that of the fourth embodiment. In the fifth embodiment, a hook portion 419 is disposed at the rear end of the screw portion 416 and protrudes toward the axis thereof, whereas the resilient element 30 is also a compressed spring. The resilient element 30 has a rear end abutting against the hook portion 419 and a front end fixed to the connector 24. The resilient element 30 directly exerts a forward elastic force on the suction member 20 by the connector 24, and indirectly exerts a reward elastic force on the base 10 by the first adjustment element 40a. The resilient element 30 generates the elastic force, under which the connector 24 is pushed to the front end of the first adjustment element 40a, such that the tongue fixing portion 22 is driven to move toward the base 10. The elastic force being both weaker than the suction force between the suction member 20 and the user's tongue and weaker than the pulling force generated by the user's tongue in tongue motion. Referring to FIG. 20 and FIG. 21, when the user rotates the first adjustment element 40a to move it forward and rearward relative to the base 10, the rear end of the resilient element 30 directly moves forward and rearward together with the first adjustment element 40a because the rear end of the resilient element 30 abuts against the hook portion 419; at this point in time, the front end and rear end of the resilient element 30 move together, and the connector 24 causes the suction member 20 to move forward and rearward together with the first adjustment element 40a, thereby adjusting the position of the user's tongue. The two ends of the resilient element 30 move simultaneously for the same distance and in the same direction as the first adjustment element 40a; thus, the extent to which the resilient element 30 is stretched or compressed does not vary in response to the movement of the first adjustment element 40a, whereas the elastic force of the resilient element 30 does not vary in response to the movement of the first adjustment element 40a. Thus, the elastic force is transmitted to the user's tongue via the suction member 20 and thus functions as the tractional force for pulling the user's tongue forward. Therefore, in this embodiment, the user's tongue is stabilized under the tractional force, such that the pull at the tongue remains unabated in the course of tongue position adjustment, thereby ensuring that the user's tongue can stay at a non-collapsed position.

Figure 22:
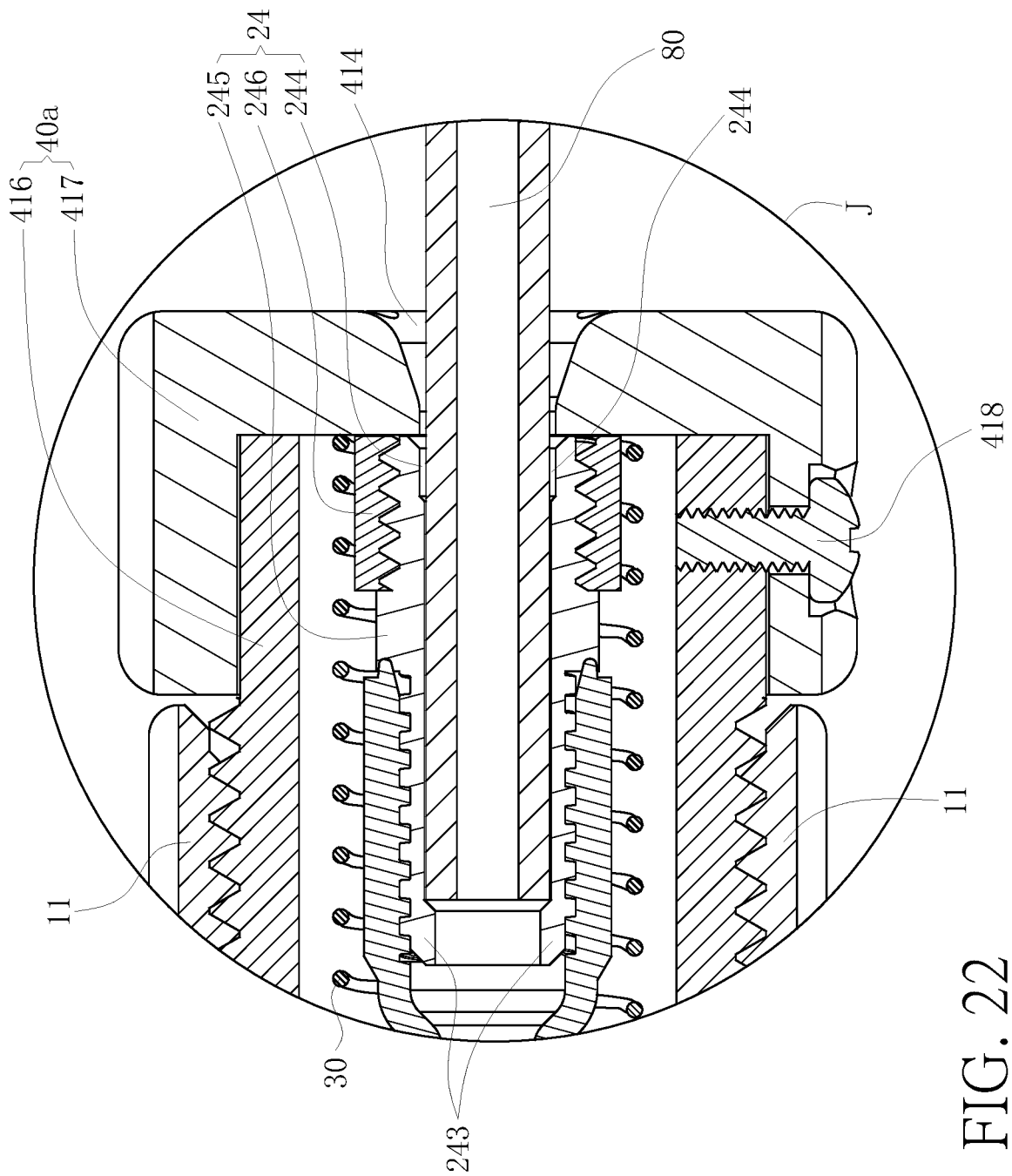
FIG. 22 is a partial enlarged view of part J in FIG. 20.

Referring to FIG. 22, the connector 24 is formed by fitting together a fitting portion 245 and a sliding portion 246 which are previously separately formed. The sliding portion 246 is contained in the first adjustment element 40a. The front end of the resilient element 30 is contained and fixed to the sliding portion 246. The front end of the sliding portion 246 functions as the third stopping portion 242 and is blocked by the operating cap 417 of the first adjustment element 40a, and adapted to limit the forward displacement of the tongue fixing portion 22. One end of the fitting portion 245 is demountably received in the sliding portion 246 and fitted to the connection pipe 80. The other end of the fitting portion 245 is fitted and fixed within the channel 21. In this embodiment, the fitting portion 245 and the sliding portion 246 are connected to each other by threads, whereas the fitting portion 245 and the channel 21 are connected to each other by threads. The threads between the fitting portion 245 and the sliding portion 246 are triangular threads with large pitches, whereas the threads between the fitting portion 245 and the channel 21 are rectangular threads with small pitches; thus, the former is easier to combine and separate than the latter. Preferably, the size of the screw portion 416 at the opening of the hook portion 419 is greater than or equal to the maximum size of the front end of the channel 21 received in the first adjustment element 40a; thus, separation of the fitting portion 245 and the sliding portion 246 causes the sliding portion 246 to stay in the first adjustment element 40a and causes the fitting portion 245 and the channel 21 to withdraw from the rear end (i.e., the end positioned proximate to the user) of the first adjustment element 40a, such that the user can change constituent parts of the suction member 20 except for the sliding portion 246 by means of the threads between the fitting portion 245 and the sliding portion 246, thereby rendering it convenient for the user to purchase related consumables and thereby independently carry out maintenance of the device. Furthermore, the channel 21 and the fitting portion 245 not only have sufficient resilience but also have slightly greater dimensions than the opening at the hook portion 419; thus, the channel 21 and the fitting portion 245 can deform and thus pass through the opening of the hook portion 419. In another embodiment, the sliding portion 246 directly abuts against the front end of the resilient element 30, and the sliding portion 246 functions as a second adjustment element for adjusting the extent to which the resilient element 30 is stretched or compressed.

Referring to FIG. 18 through FIG. 21, in this embodiment, the tongue fixing portion 22 is made of a soft material which is comfortable to the human body, such as silicone. The tongue fixing portion 22 is cup-shaped and thus matches the user's tongue in terms of outline. The tongue fixing portion 22 has a receiving space 221 which opens rearward to receive the front end of the user's tongue when the device is in use. Two concave spaces 222 for receiving the user's lingual frenulum, are disposed at the rear end of the tongue fixing portion 22 and disposed on the upper side and the lower side of the tongue fixing portion 22, respectively. Furthermore, one said concave 222 is disposed below the receiving space 221, whereas the other concave 222 is disposed above the receiving space 221. Owing to the symmetric arrangement of the two concave spaces 222, the user need not give considerations to the upward and downward orientation of the tongue fixing portion 22 while operating the device. An air inlet 223 is disposed on the inner surface of the receiving space 221, that is, the inner surface (facing the user's tongue) of the tongue fixing portion 22. The receiving space 221 is in communication with the channel 21 through the air inlet 223. Therefore, when the device is in use, the negative pressure is ultimately transferred into the receiving space 221 and applied to the user's tongue received in the receiving space 221, thereby allowing the user's tongue to be adsorbable and fixed to the tongue fixing portion 22. The tongue fixing portion 22 fittingly surrounds the transverse outline of the user's tongue to form a hermetic seal. The transverse outline is the outline of the transverse cross section of the user's tongue. The negative pressure source 50 provides a negative pressure to the user's tongue in contact with the tongue fixing portion 22. The negative pressure is transmitted to the interior of the receiving space 221 but not to the entire user's oral cavity. Furthermore, the receiving space 221 receives the user's tongue only, and thus the negative pressure acts on the user's tongue but not on the other parts of the user's head. The transverse cross section area of the bore of the channel 21 decreases toward the user's tongue (i.e., at the air inlets 223), to prevent the user's tongue from entering into the bore of the channel 21 under the suction force. In this embodiment, the tongue fixing portion 22 may move in directions perpendicular to the front-rear direction and in directions other than perpendicular to the front-rear direction.

Figure 23:
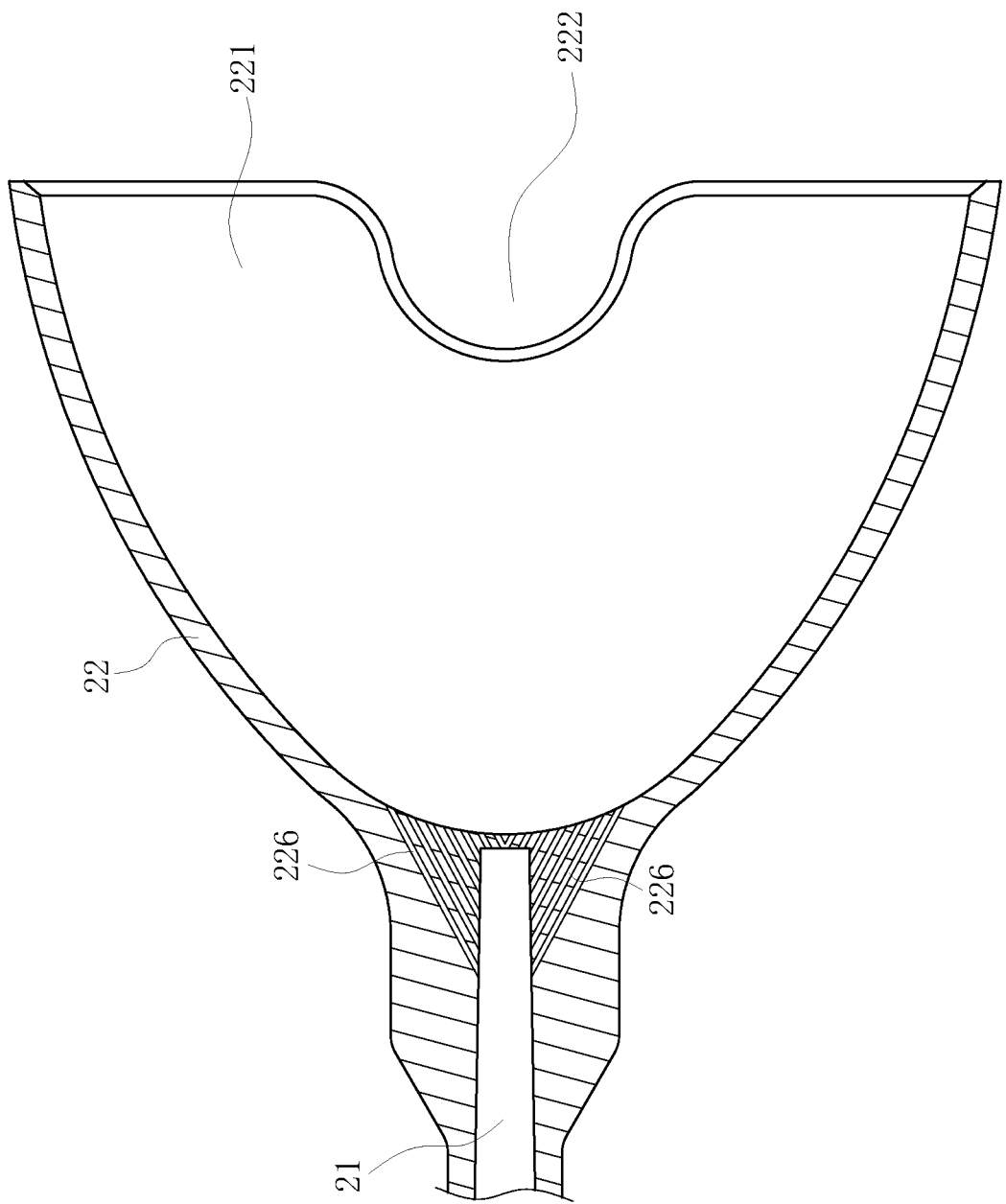
FIG. 23 is a cross-sectional view of a tongue fixing portion.
Figure 24:
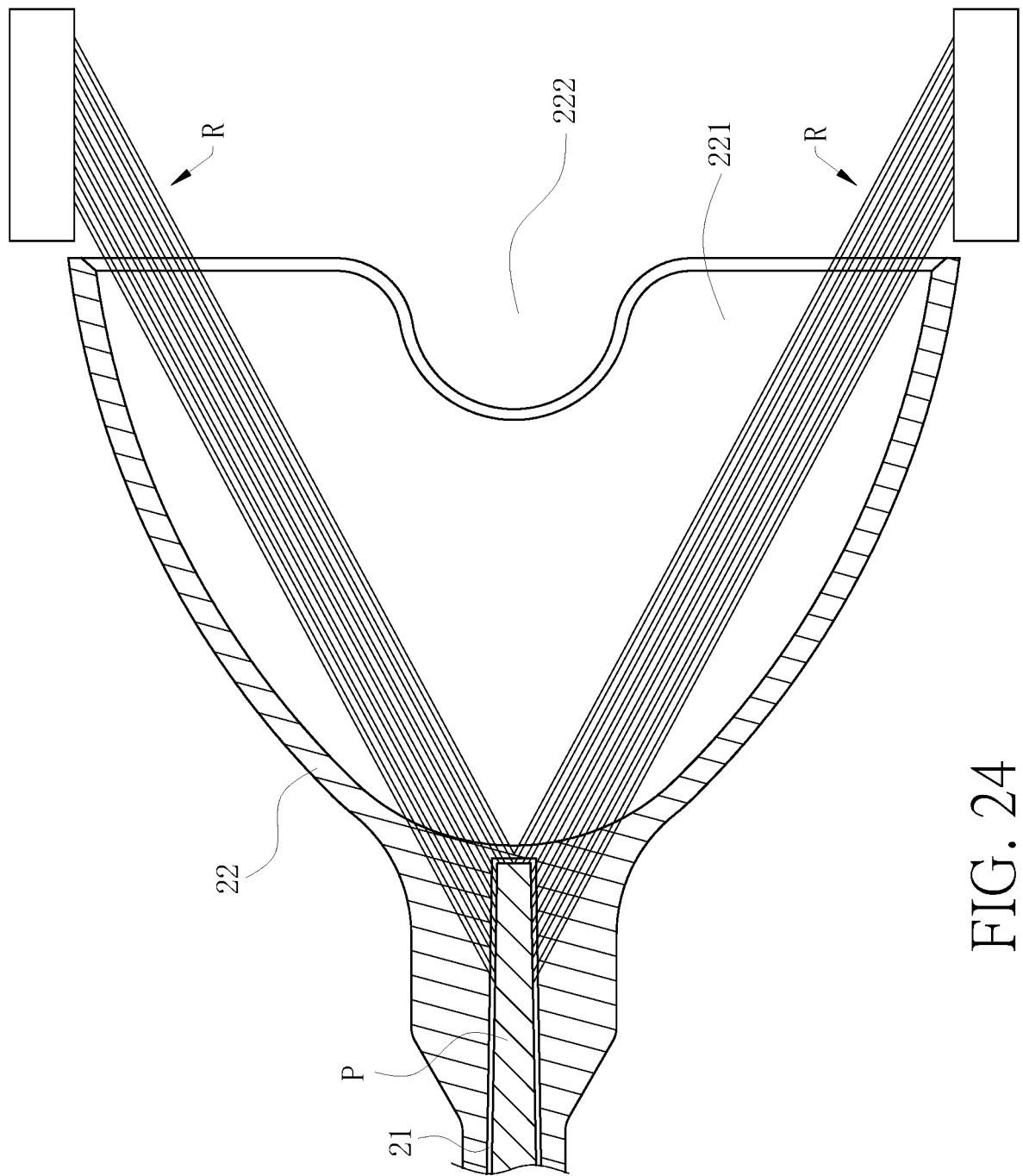
FIG. 24 is a schematic view of micro-channels shown in FIG. 23 and formed by laser drilling.

Referring to FIG. 23 and FIG. 24, in addition to providing a single air inlet 223, a plurality of micro-channels 226 communicated with channel 21 can also be provided. These micro-channels 226 and the air inlet 223 can be disposed on the tongue fixing portion 22 together, or the micro-channels 226 can replace the air inlet 223. These micro-channels 226 are formed by a drilling process performed with laser R (i.e., the laser R from the receiving space 221). The drilling process starts from the inner surface of the tongue fixing portion 22. The micro-channels 226 thus formed are densely distributed and are of the same diameter. The micro-channels 226 are arranged in rows. Each row has a plurality of said micro-channels 226. The micro-channels 226 have a diameter of 0.5 mm each, extend linearly, and run obliquely relative to the channel 21. The laser R may carry out an excessive burning process and thus damage the suction member 20; to preclude this, a protective element P is disposed in the channel 21 to stop the laser R from passing through the channel 21, and the surface of the protective element P must be treated to not reflect the laser R.

Except for the abovementioned differences, the fifth embodiment is substantially identical to the fourth embodiment and thus is, for the sake of brevity, not described further.

In all the aforesaid embodiments, the resilient element 30 serves as a driving mechanism. In another embodiment, the driving mechanism is provided in the form of a pneumatic cylinder, and the negative pressure it maintains not only directly acts on the user's tongue T to enable the user's tongue T to be fixed to the suction member 20 but also acts on the suction member 20 to pull the suction member 20 forward continuously under the negative pressure so as to pull the user's tongue T outward and preclude its collapse. In another embodiment, the user's tongue T is pulled under the negative pressure maintained not only by two means for pulling the tongue T, i.e., the elastic force of the resilient element 30 and the pneumatic cylinder, but also by a magnetic force, for example, using a solenoid valve.

Figure 25:
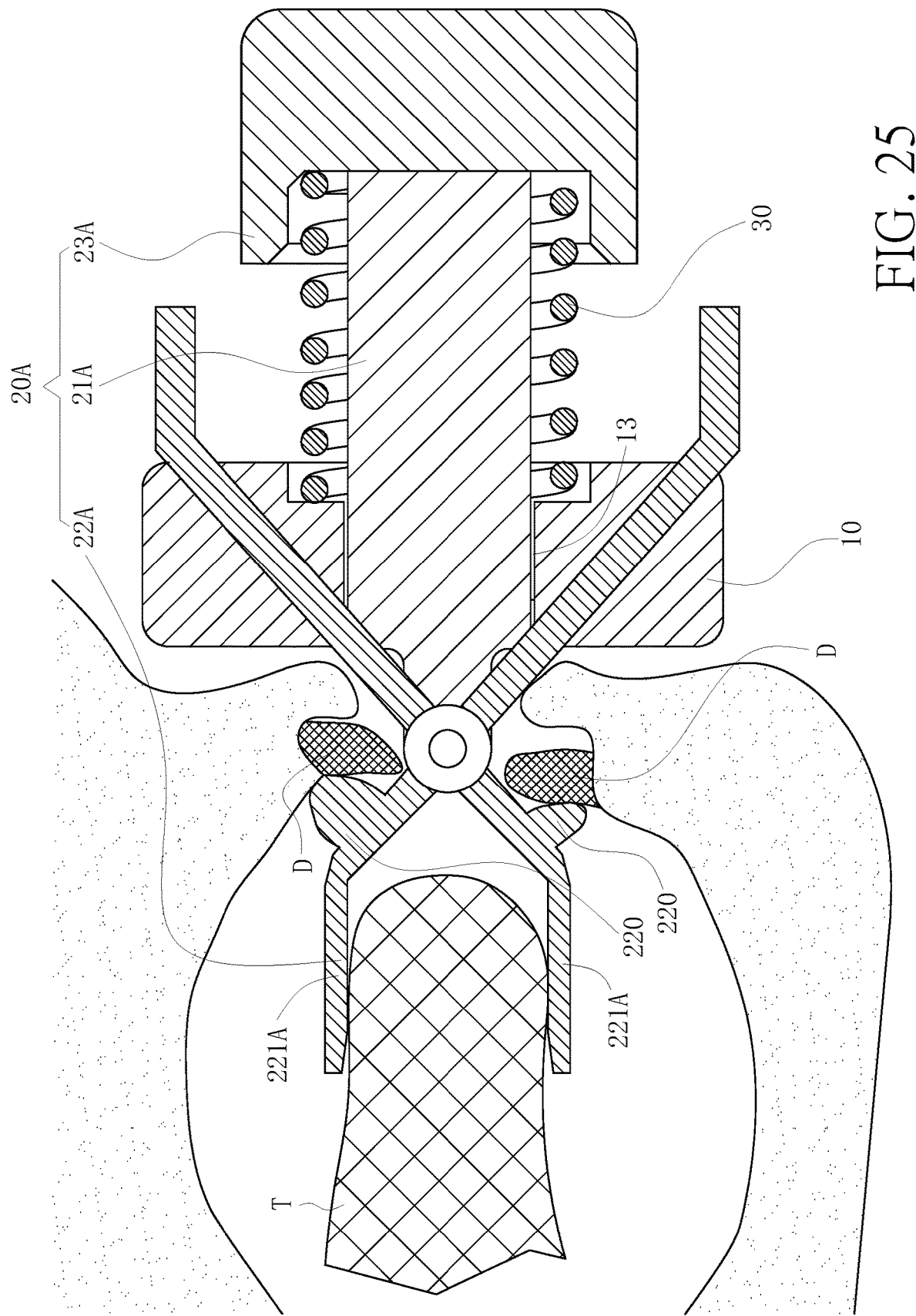
FIG. 25 is a schematic view of the device for alleviating obstructive sleep apnea according to the sixth embodiment of the present disclosure.
Figure 26:
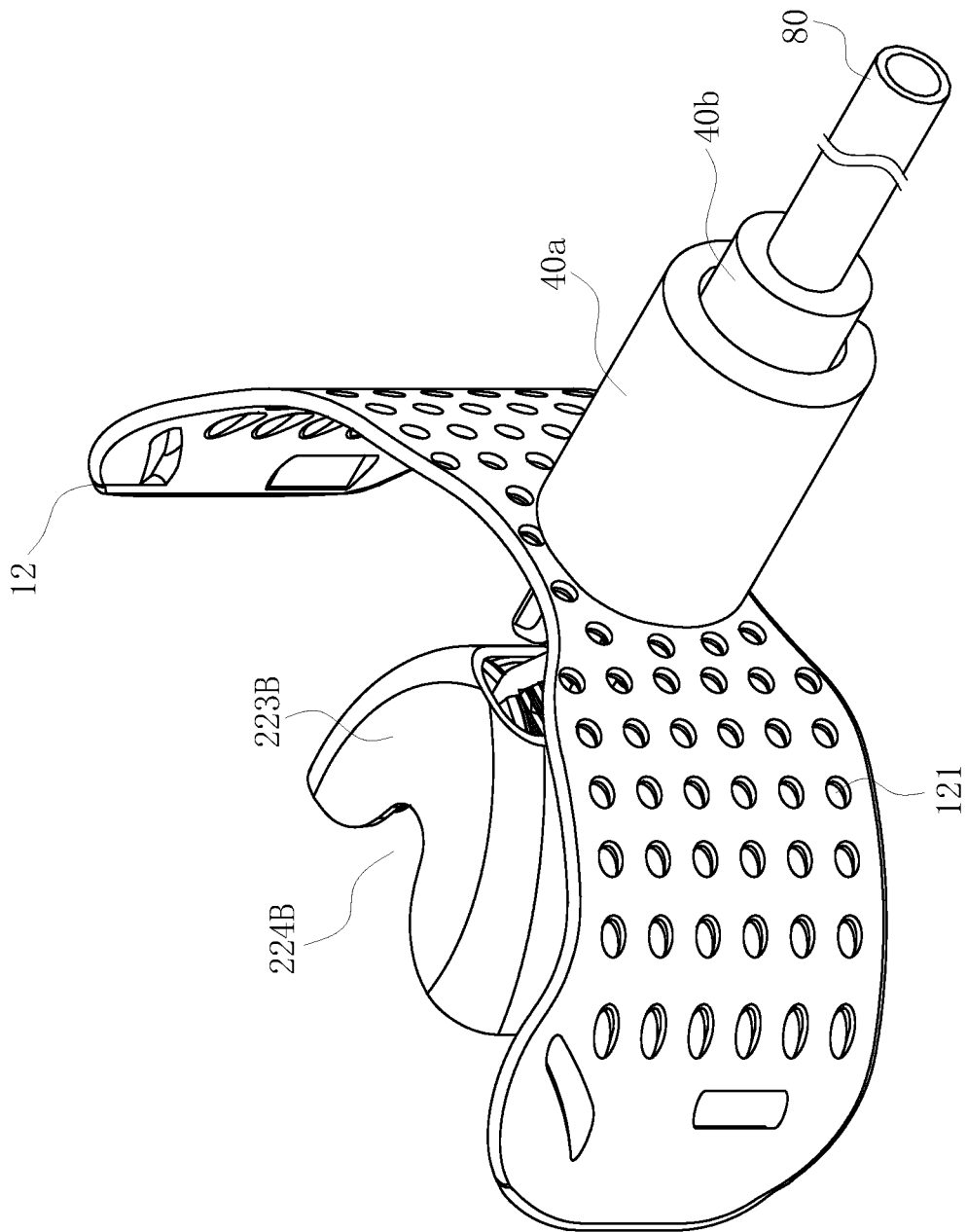
FIG. 26 is a schematic view of the device for alleviating obstructive sleep apnea according to the seventh embodiment of the present disclosure.

Referring to FIG. 25, the device for alleviating obstructive sleep apnea is provided according to the sixth embodiment of the present disclosure. The driving mechanism of the device in the sixth embodiment is similar to its counterpart in the first embodiment, pulling the user's tongue T outward under an elastic force generated by a resilient element 30. However, the device in the sixth embodiment is different from its counterpart in the first embodiment in terms of the mechanism for fixing the user's tongue T in place. The device in the sixth embodiment has the following technical features: the base 10 also has the passage 13; a link rod 21A passes through the passage 13; a pliers 22A function as the tongue fixing portion for connecting to the rear end of the link rod 21A; a front lid 23A connects to the front end of the link rod 21A; and the resilient element 30 is a compression spring fitted around the link rod 21A. The rear end of the resilient element 30 abuts against the base 10. The front end of the resilient element 30 abuts against the front lid 23A. The pliers 22A, the link rod 21A and the front lid 23A together constitute a tongue puller 20A. The front lid 23A bears the forward elastic force of the resilient element 30, and the link rod 21A transmits the elastic force to the pliers 22A such that the pliers 22A move forward relative to the base 10 and thus grip the user's tongue T from above and below to fix the user's tongue T in place, thereby allowing the user's tongue T to be pulled outward. Furthermore, in this embodiment, the front end of a holding portion 221A of the pliers 22A has two second stopping portions 220 which abut against the user's teeth D.

Referring to FIG. 26 through FIG. 29, the device for alleviating obstructive sleep apnea is provided according to the seventh embodiment of the present disclosure and comprises a base 10, a tongue puller 20B movably penetrating the base 10, a first adjustment element 40a connected to the base 10, a second adjustment element 40b connected to the tongue puller 20B, and a resilient element 30 disposed between the first adjustment element 40a and the second adjustment element 40b. The resilient element 30 functions as a driving mechanism for providing a forward elastic force to the second adjustment element 40b so as to drive the forward movement of the tongue puller 20B relative to the base 10. The tongue puller 20B has a channel 21 extending in the front-rear direction and a tongue fixing portion 22B connecting to the channel 21. The channel 21 passes through a passage 13 of the base 10. The tongue fixing portion 22B in operation enters the user's oral cavity to fix the user's tongue T in place.

Figure 27:
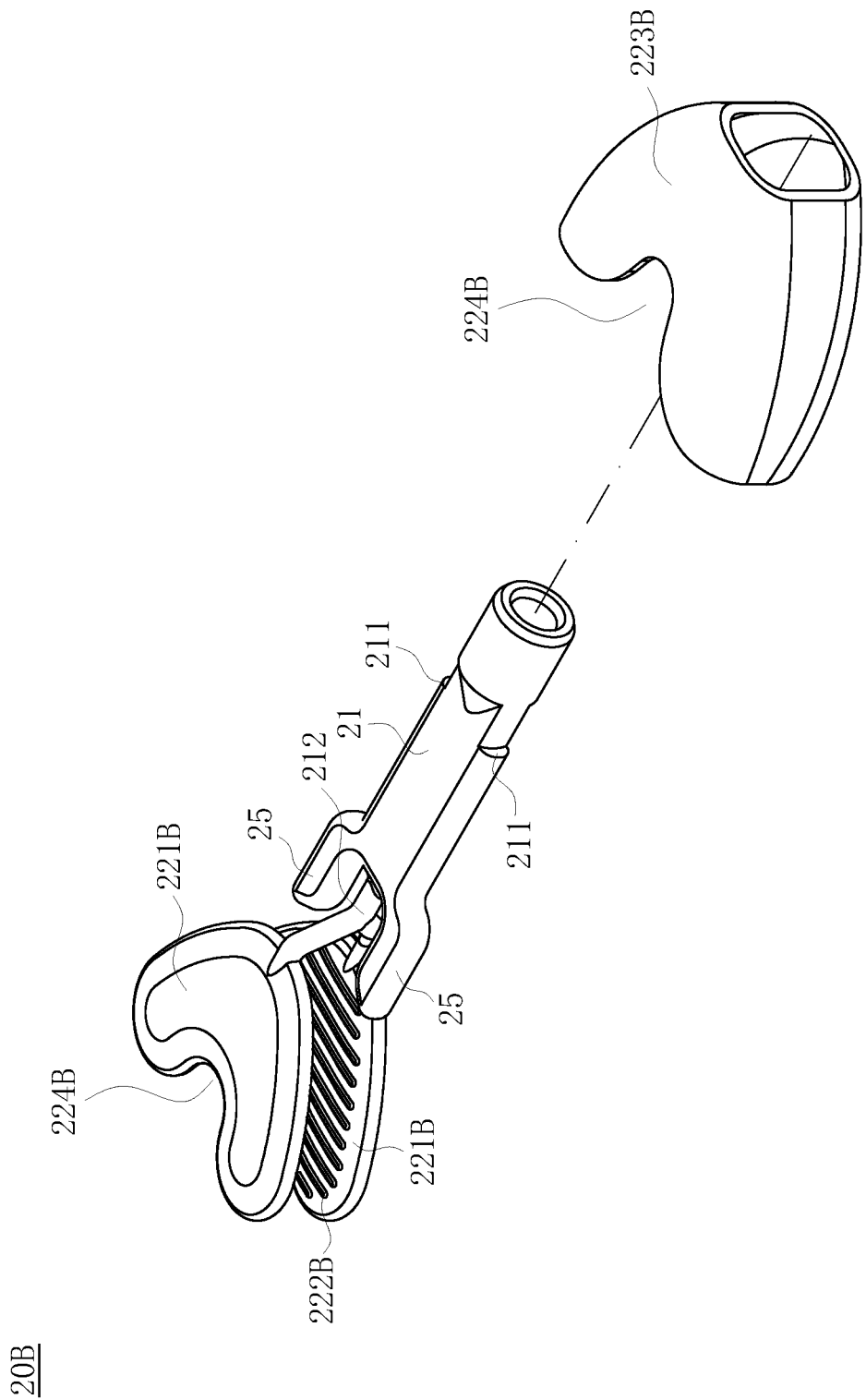
FIG. 27 is an exploded view of a tongue puller of FIG. 26.
Figure 28:
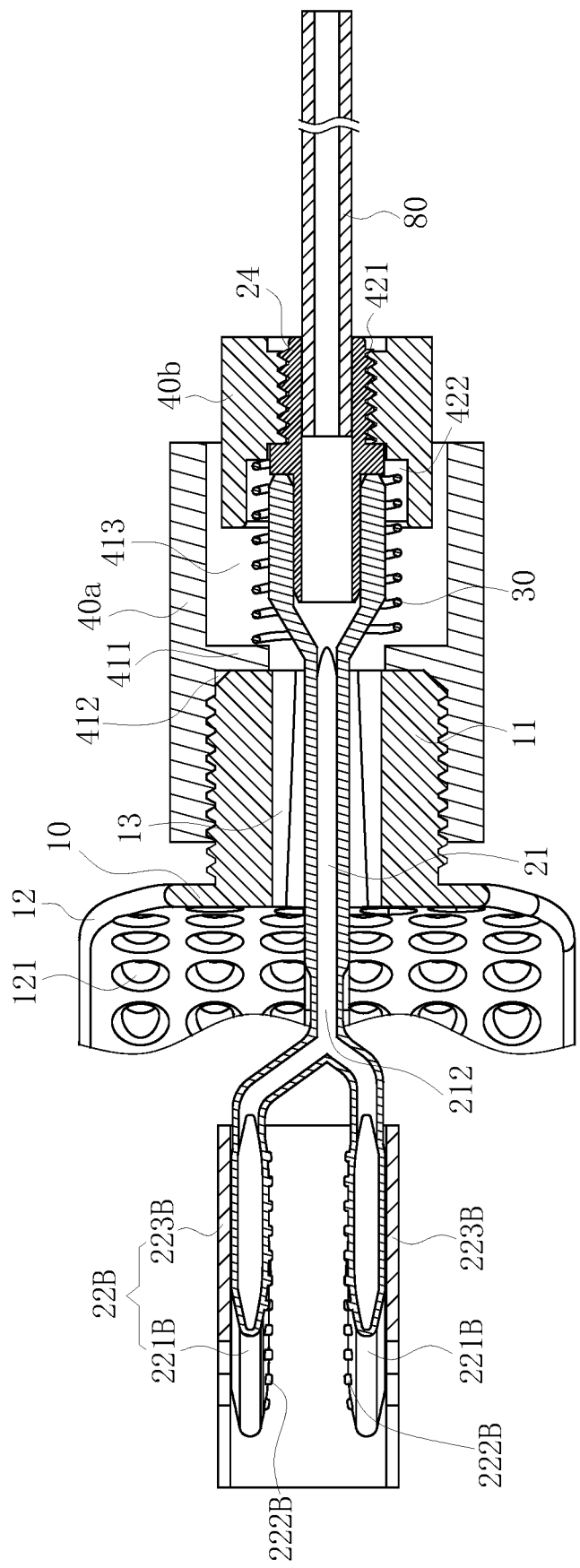
FIG. 28 is a cross-sectional view based on FIG. 26.

Referring to FIG. 27 and FIG. 28, the outer surface of the channel 21 has a first stopping portion 211. The first stopping portion 211 and the first adjustment element 40a limit the forward and rearward movement of each other, thereby limiting the outward (i.e., forward) displacement of the tongue fixing portion 22B. The rear end of the channel 21 has a softness portion 212 with a thinner wall than the other parts of the channel 21. Therefore, the softness portion 212 is softer than the other parts of the channel 21 and thus is deformable to a certain extent. The tongue fixing portion 22B has two hollow-cored holding portions 221B. The holding portions 221B are ductile and are in communication with the channel 21 through the softness portion 212. The two holding portions 221B correspond in position to each other vertically. When the device is in use, the two holding portions 221B attach to the upper surface and lower surface of the user's tongue T, respectively. The attaching surface of each holding portion 221B has a plurality of protruding ribs 222B. The protruding ribs 222B extend in the transverse direction to increase the friction between the holding portions 221B and the user's tongue T. The tongue fixing portion 22B further has a restraint hood 223B. The restraint hood 223B is resilient and capable of containing the two holding portions 221B and the user's tongue T simultaneously to prevent separation of the holding portions 221B from the user's tongue T. In this embodiment, openings 224B are concavely disposed at the rear edges of the restraint hood 223B and the holding portions 221B to accommodate the user's lingual frenulum.

Figure 29:
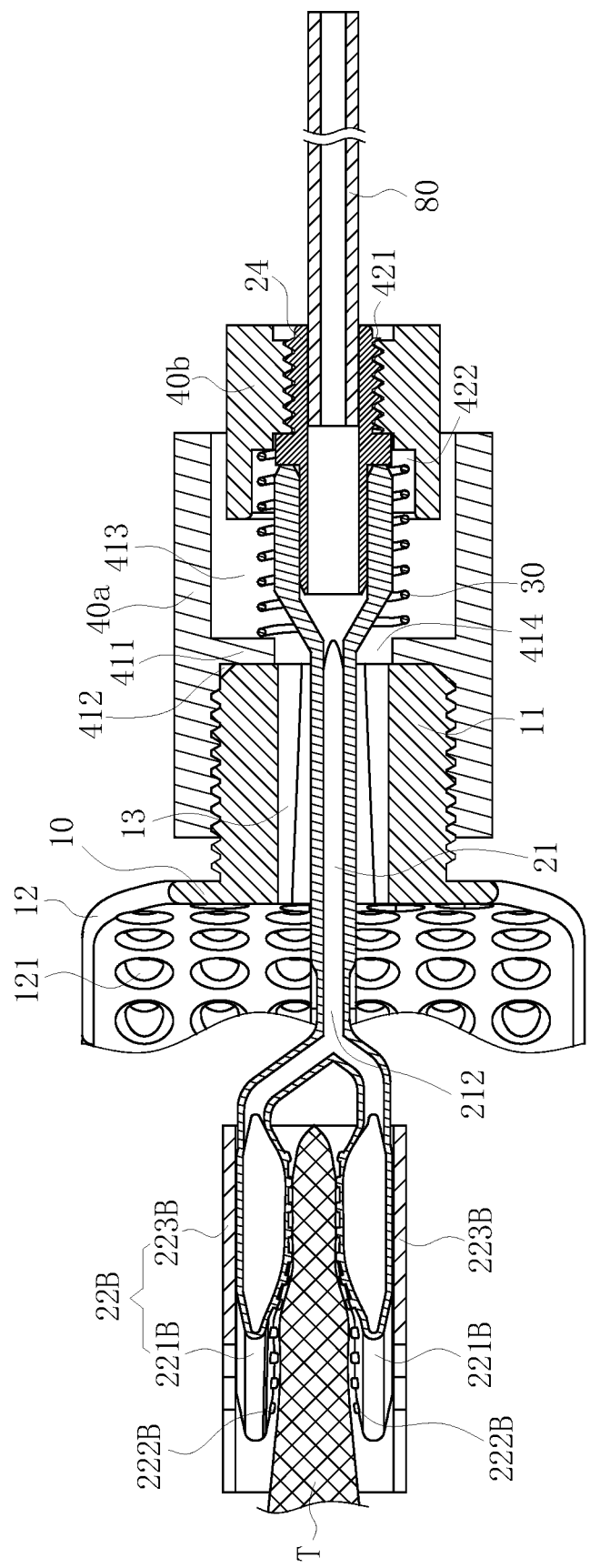
FIG. 29 is a schematic view based on FIG. 28 and indicative of an operating state.

Referring to FIG. 28 and FIG. 29, when the device is in use, the user's tongue T enters the restraint hood 223B and lies between the two holding portions 221B. In this embodiment, the holding portions 221B are in communication with an air inflator pump (not shown) through the channel 21. The holding portions 221B are inflated and thus expanded to thereby press against the user's tongue T, such that the user's tongue T is held between the two expanded holding portions 221B. Therefore, when the resilient element 30 drives the tongue puller 20B forward, the tongue fixing portion 22B pulls the user's tongue T forward so as to prevent the user's tongue T from collapsing. In another embodiment, the holding portions 221B are filled with liquid in order to be expanded.

In the sixth embodiment and the seventh embodiment, the driving force generated by the driving mechanism 30 is not only weaker than the tractional force exerted by the tongue pullers 20A, 20B on the user's tongue T but is also weaker than the pulling force generated by the user's tongue T in tongue motion.

The device for alleviating obstructive sleep apnea according to the present disclosure has advantages as follows:

1. The suction member 20 or the tongue pullers 20A, 20B are disposed at the stopping portions such that the device can prevent the collapse of the user's tongue T without pulling the user's tongue T beyond the user's lips L, so as to not pull the user's tongue T excessively and cause the user discomfort.

2. The device prevents the collapse of the user's tongue T while allowing the user to appropriately move the tongue T, such as moving the tongue T rearward to facilitate the swallowing of saliva and thereby preventing the accumulation of saliva. After the user has finished moving the tongue T, the device is effective in automatically restoring the tongue T to a non-collapsed position under an elastic force generated by the resilient element 30, the negative pressure in the pneumatic cylinder, or an attracting magnetic force.

3. In some embodiments, the first adjustment element 40a and the second adjustment element 40b allow the user convenience in adjusting the strength of the elastic force provided by the resilient element 30 and thus in adjusting the pulling force generated by the tongue T.

4. In some embodiments, the micro-channels 226 and the protective pad 23 distribute the suction force exerted on the tongue T under the negative pressure and thus preclude the user's discomfort.

5. In some embodiments, the outer expansion portion 12 has a plurality of perforations 121 for preventing the outer expansion portion 12 from hermetically sealing the user's mouth, such that a user who has difficulty in breathing through the nose, such as a patient with nasal congestion, can breathe through the mouth.

6. In some embodiments, the occlusion portion 60 is disposed between the user's upper teeth D and lower teeth D, and the occlusion portion 60 has greater hardness than the suction member 20 so as to prevent the user from biting the tongue T which might otherwise happen because of any excessive biting force exerted on the suction member 20 and the tongue T fixed to the suction member 20.

7. In some embodiments, when the user rotates the first adjustment element 40a to move the first adjustment element 40a forward and rearward relative to the base 10, the rear end of the resilient element 30 directly moves forward and rearward together with the first adjustment element 40a because the rear end of the resilient element 30 abuts against the hook portion 419; at this point in time, the front end and rear end of the resilient element 30 move together, and the connector 24 causes the suction member 20 to move forward and rearward together with the first adjustment element 40a, thereby adjusting the position of the user's tongue. The two ends of the resilient element 30 move simultaneously for the same distance and in the same direction as the first adjustment element 40a; thus, the extent to which the resilient element 30 is stretched or compressed does not vary in response to the movement of the first adjustment element 40a, and the elastic force of the resilient element 30 does not vary in response to the movement of the first adjustment element 40a. Thus, the elastic force is transmitted to the tongue T through the suction member 20 to function as the tractional force for pulling the tongue T forward. Therefore, in this embodiment, the tongue T is stabilized under the tractional force to prevent slackening of the pull on the tongue T during the process of adjusting the position of the tongue T, so as to ensure that the tongue T can stay at a non-collapsed position.

The present disclosure is disclosed above in preferred embodiments, but the preferred embodiments are not restrictive of the claims of the present disclosure. All equivalent technical changes made to the preferred embodiments in accordance with the accompanying drawings and specification of the present disclosure shall be deemed to fall within the claims of the present disclosure.

What is claimed is:

1. A device for alleviating obstructive sleep apnea, configured to be applied to a user's head, the device comprising: a base configured to be fitted and fixed to the user's head and the base having a passage; a suction member having a hollow-cored channel extending and passing through the passage to enter the user's oral cavity and undergo displacement within the passage, with the channel connected to a tongue fixing portion, the tongue fixing portion being cup-shaped and configured to match a transverse outline of the user's tongue, forming a receiving space in communication with the channel and adapted to enclose and receive the user's tongue, wherein the suction member further has a stopping portion configured to be disposed outside the user's oral cavity to limit forward displacement of the tongue fixing portion, wherein the tongue fixing portion is adapted to, under a negative pressure, adsorb to a front end of the tongue and fittingly surround the transverse outline of the user's tongue to form a hermetic seal, such that the negative pressure is configured to act only on the user's tongue, wherein the tongue fixing portion is adapted to move freely together with the user's tongue within the user's oral cavity, wherein, when the user's tongue relaxes, the tongue fixing portion is configured to drive the user's tongue to move forward until the stopping portion stops moving, a resilient element for providing the tongue fixing portion with an elastic force required to approach the base, the elastic force configured to be not only weaker than a suction force between the suction member and the user's tongue but also weaker than a pulling force configured to be generated by the user's tongue in tongue motion; a negative pressure source in communication with the channel and adapted to provide the negative pressure to the user's tongue in contact with the tongue fixing portion; and an adjustment element configured to be disposed outside the user's oral cavity, connected to the base, and capable of moving forward and rearward relative to the base, wherein the resilient element is received in the adjustment element, and the resilient element has an end connected to the adjustment element, wherein an extent to which the resilient element is stretched or compressed remains unchanged in the course of forward and rearward movement of the adjustment element relative to the base.

2. A device for alleviating obstructive sleep apnea, comprising: a base configured to be fitted and fixed to a user's head and the base having a passage; a suction member having a channel extending and passing through the passage to enter the user's oral cavity and undergo displacement within the passage, with the channel connected to a tongue fixing portion, the tongue fixing portion configured to be disposed at a front end of the user's tongue, wherein the suction member has a stopping portion for limiting forward displacement of the tongue fixing portion; a resilient element for providing the tongue fixing portion with an elastic force required to approach the base, the elastic force configured to be both weaker than a suction force between the suction member and the user's tongue and weaker than a pulling force configured to be generated by the user's tongue in tongue motion; a negative pressure source in communication with the channel and configured to provide a negative pressure to the user's tongue in contact with the tongue fixing portion; and an adjustment element configured to be disposed outside the user's oral cavity, connected to the base, and capable of moving forward and rearward relative to the base, wherein the resilient element is received in the adjustment element, and the resilient element has an end connected to the adjustment element, wherein an extent to which the resilient element is stretched or compressed remains unchanged in the course of forward and rearward movement of the adjustment element relative to the base.

3. The device for alleviating obstructive sleep apnea according to claim 2, wherein the suction member comprises a connector in communication with the channel and the negative pressure source, and the end of the resilient element connected to the adjustment element exerts a force on the adjustment element and the resilient element comprises another end exerting a force on the connector.

4. The device for alleviating obstructive sleep apnea according to claim 3, wherein the connector, the resilient element and the channel are at least partially received in the adjustment element simultaneously.

5. The device for alleviating obstructive sleep apnea according to claim 4, wherein the resilient element fits around the channel, and at least part of the resilient element is closer to the adjustment element than is the channel so as to prevent the resilient element from interfering with the channel.

6. The device for alleviating obstructive sleep apnea according to claim 3, wherein the connector and the channel are connected by threads.

7. The device for alleviating obstructive sleep apnea according to claim 3, wherein the stopping portion is disposed at the connector.

8. The device for alleviating obstructive sleep apnea according to claim 2, wherein the tongue fixing portion has a receiving space in communication with the channel, such that the user's tongue is configured to be at least partially received in the receiving space, starting from the front end of the user's tongue.

9. The device for alleviating obstructive sleep apnea according to claim 8, wherein a concave space is formed at a rear end of the tongue fixing portion to accommodate a lingual frenulum of the user.

10. The device for alleviating obstructive sleep apnea according to claim 9, wherein the tongue fixing portion further comprises two concave spaces disposed on an upper side and a lower side of the tongue fixing portion, respectively.

11. The device for alleviating obstructive sleep apnea according to claim 2, wherein the base comprises an outer expansion portion configured to be disposed outside the user's oral cavity, and the outer expansion portion is of dimensions configured to be greater than dimensions of the user's mouth.

12. The device for alleviating obstructive sleep apnea according to claim 11, wherein the outer expansion portion has a plurality of perforations penetrating an outer surface of the outer expansion portion, configured to be away from the user's face, and penetrating an inner surface of the outer expansion portion, configured to be facing the user's face.

13. The device for alleviating obstructive sleep apnea according to claim 11, wherein the outer expansion portion is configured to abut against the user's face except for the user's lips and the outer expansion portion comprises a main body adapted to cover the user's face and a pad disposed on the main body, the pad configured to be disposed between the main body and the user's face when in use, wherein the pad is elastically stretched and contracted relative to the main body.

14. The device for alleviating obstructive sleep apnea according to claim 2, wherein the tongue fixing portion has an air inlet, the air inlet configured to be disposed on an inner surface of the tongue fixing portion, facing the user's tongue, and being in communication with the channel, and the negative pressure is configured to act on the front end of the user's tongue through the air inlet, thereby allowing at least a portion of the user's tongue to attach to the inner surface of the tongue fixing portion.

15. The device for alleviating obstructive sleep apnea according to claim 2, wherein the resilient element directly exerts a forward elastic force on the suction member, and indirectly exerts a rearward elastic force on the base.

16. The device for alleviating obstructive sleep apnea according to claim 2, wherein the adjustment element comprises a screw portion received in the passage, the screw portion being penetrated in a front-rear direction so as to receive the resilient element and a portion of the suction member, and the end of the resilient element connected to the adjustment element exerts a force on a rear end of the screw portion, wherein the adjustment element further comprises an operating cap fixed to a front end of the screw portion such that the stopping portion and the operating cap abut against each other.

17. The device for alleviating obstructive sleep apnea according to claim 2, wherein the tongue fixing portion moves in a direction perpendicular to a front-rear direction and in directions other than perpendicular to the front-rear direction.

18. The device for alleviating obstructive sleep apnea according to claim 2, wherein a transverse cross-section area of a bore of the channel is configured to decrease toward the user's tongue to prevent the user's tongue from entering the bore of the channel under the suction force.

* * * * *